United States Patent [19]
Garen et al.

[11] Patent Number: 6,140,470
[45] Date of Patent: Oct. 31, 2000

[54] HUMAN MONOCLONAL ANTI-TUMOR ANTIBODIES

[75] Inventors: Alan Garen, New Haven, Conn.; Xiaohang Cai, Chicago, Ill.

[73] Assignee: Yale University, New Haven, Conn.

[21] Appl. No.: 08/983,607

[22] PCT Filed: Jun. 28, 1996

[86] PCT No.: PCT/IB96/01032

§ 371 Date: Apr. 27, 1998

§ 102(e) Date: Apr. 27, 1998

[87] PCT Pub. No.: WO97/02479

PCT Pub. Date: Jan. 23, 1997

Related U.S. Application Data

[63] Continuation-in-part of application No. 08/497,647, Jun. 30, 1995, abandoned.

[51] Int. Cl.[7] .................................................... C07K 16/00
[52] U.S. Cl. .................................. 530/387.1; 530/388.1; 530/388.15; 530/388.2; 530/350
[58] Field of Search ................................ 435/91.4, 320.1, 435/0.6; 530/387.1, 388.1, 388.15, 388.2

[56] References Cited

U.S. PATENT DOCUMENTS

| | | |
|---|---|---|
| 4,752,659 | 6/1988 | Terasaki et al. . |
| 4,865,998 | 9/1989 | Feickert et al. . |
| 5,091,513 | 2/1992 | Huston et al. . |

FOREIGN PATENT DOCUMENTS

WO 94/26878  11/1994  WIPO .

OTHER PUBLICATIONS

Kieber–Emmons et al (Lupus, 3:379–392), 1994.
Cai, X., & Gren, A., *P.N.A.S. USA* 93: 66280–6285 (1996).
Cai, X., &Garen, A., *P.N.A.S.*94: 9261–9266 (1997).
Dranoff, G., & Mulligan, R.C., *Adv. Immunol.*58: 417–455 (1950).
Griffiths, A.D., et al., *EMBO J.*12: 725–734 (1993).
Ghetie, M.–A., & Vitta, E.S., *Curr. Opin. Immunol.*6: 707–714 (1994).
Hall, B.L., et al., *Cancer Res.*54: 5178–5185 (1994).
Hoon, D.S.B., et al., *Cancer Res.*53: 5244–5250 (1993).
Marks, J.D., et al., *Biotechnology* 10: 779–783 (1992).
Marks, J.D., et al., *J. Mol. Biol.*222: 581–597 (1991).
Scott, J.K., & Smith, G.P., *Science*249: 386–389 (1990).
Wilmes, E., et al., *Laryng. Rhinol. Otol.*66: 144–148 (1987).
Winter, G., & Milstein, C., *Nature* 349: 293–299 (1991).

*Primary Examiner*—Susan Ungar
*Attorney, Agent, or Firm*—Mary M. Krinsky

[57] ABSTRACT

Human monoclonal anti-tumor antibodies are isolated from fusion phage single-chain Fv and $V_H$ antibody libraries constructed from the peripheral blood lymphocytes of immunized cancer patients. Antibodies that bind to tumor cells of the same kind as the patient's are selected, and antibodies that also bind to a human normal cell type are removed. The remaining fusion phage antibodies are cloned and then are tested for binding to at least two normal human cell types. Antibodies that fail to bind to the normal cells are further tested for binding to a panel of tumor cells, typically including the original tumor type and several related and unrelated tumors. Human monoclonal antibodies that bind specifically to the original tumor or also to some other tumors, or that bind to the original tumor and cells from the same developmental lineage, are obtained and sequenced. The selected antibodies can be used to design molecules which are potentially useful for various diagnostic and therapeutic purposes. The single-chain Fv and $V_H$ libraries from cancer patients are also being used to select antibodies against other targets, such as endothelial cells, which have diagnostic and clinical applications.

16 Claims, No Drawings

```
                          SEQUENCE LISTING (1) GENERAL INFORMATION:

(iii) NUMBER OF SEQUENCES:  51

(2) INFORMATION FOR SEQ ID NO:1:

(i) SEQUENCE CHARACTERISTICS:
              (A) LENGTH:  24 residues
              (B) TYPE: nucleic acid
              (C) STRANDEDNESS: single
              (D) TOPOLOGY: linear (ii) MOLECULE TYPE:  DNA
              (A) DESCRIPTION: primer used in constructs (x) PUBLICATION INFORMATION:
              (A) AUTHORS:  Marks, J.D., et al.
              (B) TITLE:  "By-passing Immuization"
              (C) JOURNAL:  J. Mol. Biol.
              (D) VOLUME:  222
              (E) PAGES:  581-597; primer on page 584
                  (denoted HuIgG1-4CH1FOR)

(xi) SEQUENCE DESCRIPTION: SEQ ID NO:1:

GTCCACCTTG GTGTTGCTGG GCTT                                        24

(2) INFORMATION FOR SEQ ID NO:2:

(i) SEQUENCE CHARACTERISTICS:
              (A) LENGTH:  24 residues
              (B) TYPE: nucleic acid
              (C) STRANDEDNESS: single
              (D) TOPOLOGY: linear (ii) MOLECULE TYPE:  DNA
              (A) DESCRIPTION: primer used in constructs (x) PUBLICATION INFORMATION:
              (A) AUTHORS:  Marks, J.D., et al.
              (B) TITLE:  "By-passing Immuization"
              (C) JOURNAL:  J. Mol. Biol.
              (D) VOLUME:  222
              (E) PAGES:  581-597; primer on page 584
                  (denoted HuIgMFOR)

(xi) SEQUENCE DESCRIPTION: SEQ ID NO:2:

TGGAAGAGGC ACGTTCTTTT CTTT                                        24

(2) INFORMATION FOR SEQ ID NO:3:
```

-continued

```
    (i) SEQUENCE CHARACTERISTICS:
         (A) LENGTH:  24 residues
         (B) TYPE: nucleic acid
         (C) STRANDEDNESS: single
         (D) TOPOLOGY: linear (ii) MOLECULE TYPE:  DNA
         (A) DESCRIPTION: primer used in constructs (x) PUBLICATION INFORMATION:
         (A) AUTHORS:  Marks, J.D., et al.
         (B) TITLE:  "By-passing Immuization"
         (C) JOURNAL:  J. Mol. Biol.
         (D) VOLUME:  222
         (E) PAGES:  581-597; primer on page 584
             (denoted HuGkFOR)

(xi) SEQUENCE DESCRIPTION: SEQ ID NO:3:

AGACTCTCCC CTGTTGAAGC TCTT                                          24

(2) INFORMATION FOR SEQ ID NO:4:

(i) SEQUENCE CHARACTERISTICS:
         (A) LENGTH:  27 residues
         (B) TYPE: nucleic acid
         (C) STRANDEDNESS: single
         (D) TOPOLOGY: linear (ii) MOLECULE TYPE:  DNA
         (A) DESCRIPTION: primer used in constructs (x) PUBLICATION INFORMATION:
         (A) AUTHORS:  Marks, J.D., et al.
         (B) TITLE:  "By-passing Immuization"
         (C) JOURNAL:  J. Mol. Biol.
         (D) VOLUME:  222
         (E) PAGES:  581-597; primer on page 584
             (denoted HuG^FOR)

(xi) SEQUENCE DESCRIPTION: SEQ ID NO:4:

TGAAGATTCT GTAGGGGCCA CTGTCTT                                       27

(2) INFORMATION FOR SEQ ID NO:5:

(i) SEQUENCE CHARACTERISTICS:
         (A) LENGTH:  50 residues
         (B) TYPE: nucleic acid
         (C) STRANDEDNESS: single
         (D) TOPOLOGY: linear (ii) MOLECULE TYPE:  DNA
         (A) DESCRIPTION: primer used in constructs (xi) SEQUENCE DESCRIPTION: SEQ ID NO:5:

ATGGCTCAGG GTTCGGCCGA CGTGGCCCAG GTRCAGCTGS WGSAGTCKGG              50

(2) INFORMATION FOR SEQ ID NO:6:

(i) SEQUENCE CHARACTERISTICS:
         (A) LENGTH:  50 residues
         (B) TYPE: nucleic acid
         (C) STRANDEDNESS: single
         (D) TOPOLOGY: linear (ii) MOLECULE TYPE:  DNA
         (A) DESCRIPTION: primer used in constructs (xi) SEQUENCE DESCRIPTION: SEQ ID NO:6:

ATGGCTCAGG GTTCGGCCGA CGTGGCCCAG GTCAACTTAA GGGAGTCTGG              50

(2) INFORMATION FOR SEQ ID NO:7:
```

(i) SEQUENCE CHARACTERISTICS:
    (A) LENGTH: 50 residues
    (B) TYPE: nucleic acid
    (C) STRANDEDNESS: single
    (D) TOPOLOGY: linear (ii) MOLECULE TYPE: DNA
    (A) DESCRIPTION: primer used in constructs (xi) SEQUENCE DESCRIPTION: SEQ ID NO:7:

ATGGCTCAGG GTTCGGCCGA CGTGGCCGAG GTGCAGCTGK TGSAGTCTGS          50

(2) INFORMATION FOR SEQ ID NO:8:

(i) SEQUENCE CHARACTERISTICS:
        (A) LENGTH: 59 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:8:

GGCTCGGGCG GTGGTGGGTC GGGTGGCGGC GGATCTGACA TCSWGATGAC          50

CCAGTCTCC                                                       59

(2) INFORMATION FOR SEQ ID NO:9:

(i) SEQUENCE CHARACTERISTICS:
        (A) LENGTH: 59 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:9:

GGCTCGGGCG GTGGTGGGTC GGGTGGCGGC GGATCAGAWR TTGTGMTGAC          50

KCAGTCTCC                                                       59

(2) INFORMATION FOR SEQ ID NO:10:

(i) SEQUENCE CHARACTERISTICS:
        (A) LENGTH: 59 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:10:

GGCTCGGGCG GTGGTGGGTC GGGTGGCGGC GGATCAGAAA CGACACTCAC          50

GCAGTCTCC                                                       59

(2) INFORMATION FOR SEQ ID NO:11:

(i) SEQUENCE CHARACTERISTICS:
        (A) LENGTH: 59 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:11:

GGCTCGGGCG GTGGTGGGTC GGGTGGCGGC GGATCACAGT CTGYSYTGAC        50

KCAGCCGCC                                                    59

(2) INFORMATION FOR SEQ ID NO:12:

(i) SEQUENCE CHARACTERISTICS:
        (A) LENGTH:  59 residues
        (B) TYPE: nucleic acid
        (C) STRANDEDNESS: single
        (D) TOPOLOGY: linear (ii) MOLECULE TYPE:  DNA
        (A) DESCRIPTION: primer used in constructs (xi) SEQUENCE DESCRIPTION: SEQ ID NO:12:

GGCTCGGGCG GTGGTGGGTC GGGTGGCGGC GGATCATCYT MTGWGCTGAC        50

TCAGSMACC                                                    59

(2) INFORMATION FOR SEQ ID NO:13:

(i) SEQUENCE CHARACTERISTICS:
        (A) LENGTH:  59 residues
        (B) TYPE: nucleic acid
        (C) STRANDEDNESS: single
        (D) TOPOLOGY: linear (ii) MOLECULE TYPE:  DNA
        (A) DESCRIPTION: primer used in constructs (xi) SEQUENCE DESCRIPTION: SEQ ID NO:13:

GGCTCGGGCG GTGGTGGGTC GGGTGGCGGC GGATCACASG YTRTACTGAC        50

TCAACCGYC                                                    59

(2) INFORMATION FOR SEQ ID NO:14:

(i) SEQUENCE CHARACTERISTICS:
        (A) LENGTH:  60 residues
        (B) TYPE: nucleic acid
        (C) STRANDEDNESS: single
        (D) TOPOLOGY: linear (ii) MOLECULE TYPE:  DNA
        (A) DESCRIPTION: primer used in constructs (xi) SEQUENCE DESCRIPTION: SEQ ID NO:14:

GCCACCCGAC CCACCACCGC CCGAGCCACC GCCACCTGAR GAGACGGTGA        50

CCRKKGTYCC                                                   60

(2) INFORMATION FOR SEQ ID NO:15:

(i) SEQUENCE CHARACTERISTICS:
        (A) LENGTH: 51 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:15:

AGTCTAACGT TCGGCCCCAG CGGCCCCACG TTTGATYTCC ASCTTGGTCC C      51

(2) INFORMATION FOR SEQ ID NO:16:

(i) SEQUENCE CHARACTERISTICS:
        (A) LENGTH: 51 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:16:

AGTCTAACGT TCGGCCCCAG CGGCCCCACG TTTKATMTCC ASYYKKGTCC C         51

(2) INFORMATION FOR SEQ ID NO:17:

(i) SEQUENCE CHARACTERISTICS:
        (A) LENGTH: 51 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:17:

AGTCTAACGT TCGGCCCCAG CGGCCCCACC TARRACGGTS ASCTKGGTCC C         51

(2) INFORMATION FOR SEQ ID NO:18:

(i) SEQUENCE CHARACTERISTICS:
        (A) LENGTH: 23 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:18:

ATTATTATTC GCAATTCCTT TAG                                        23

(2) INFORMATION FOR SEQ ID NO:19:

(i) SEQUENCE CHARACTERISTICS:
        (A) LENGTH: 24 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:19:

GAATTTTCTG TATGAGGTTT TGCT                                       24

(2) INFORMATION FOR SEQ ID NO:20:

(i) SEQUENCE CHARACTERISTICS:
        (A) LENGTH: 121 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes

```
        (vii) IMMEDIATE SOURCE:
              (A) LIBRARY: DM414 scFv antibodies obtained from
                  fUSE5 fusion phage construct
              (D) CLONE: H18

(ix) FEATURE:
              (A) NAME/KEY: heavy chain (xi) SEQUENCE DESCRIPTION: SEQ ID NO:20:

Glu Val Gln Leu Leu Glu Ser Gly Ala Glu Val Lys Lys Pro Gly
                 5                  10                  15

Ala Ser Val Lys Ile Ser Cys Lys Val Ser Gly His Pro Phe Thr
            20                  25                  30

Asn His Trp Phe His Trp Val Arg Gln Ala Pro Gly Gln Gly Leu
            35                  40                  45

Glu Trp Met Gly Trp Val Ser Pro Asn Thr Gly Ala Thr Lys Tyr
            50                  55                  60

Ala Glu Asn Phe Gln Gly Arg Val Thr Asn Thr Trp Asp Thr Ser
            65                  70                  75

Ile Leu Thr Ala Tyr Met Glu Leu Arg Ser Leu Thr Ser Glu Asp
            80                  85                  90

Thr Ala Val Tyr Tyr Cys Ala Ala Ala Gly Ser Ser Tyr Tyr
            95                 100                 105

Phe Gly Met Asp Ile Trp Ala Lys Gly Ile Pro Val Thr Val Ser
               110                 115                 120

Ser (2) INFORMATION FOR SEQ ID NO:21:

(i) SEQUENCE CHARACTERISTICS:
              (A) LENGTH: 111 residues
              (B) TYPE: amino acid
              (C) STRANDEDNESS: single
              (D) TOPOLOGY: linear (ii) MOLECULE TYPE:
              (A) DESCRIPTION: polypeptide (vi) ORIGINAL SOURCE:
              (A) ORGANISM: Homo sapiens (melanoma patient immu-
                  nized with autologous tumor cells)
              (B) INDIVIDUAL ISOLATE: peripheral blood lymphocytes (vii) IMMEDIATE SOURCE:
              (A) LIBRARY: DM414 scFv antibodies obtained from
                  fUSE5 fusion phage construct
              (D) CLONE: H18

(ix) FEATURE:
              (A) NAME/KEY: light chain (xi) SEQUENCE DESCRIPTION: SEQ ID NO:21:

Ser Tyr Glu Leu Thr Gln Gln Pro Ser Ala Ser Gly Thr Pro Gly
                 5                  10                  15

Gln Arg Val Thr Ile Ser Cys Ser Gly Ser Ser Ser Asn Ile Gly
            20                  25                  30

Ser Asn Tyr Val Tyr Trp Tyr Gln Gln Leu Pro Gly Thr Ala Pro
            35                  40                  45

Lys Leu Leu Ile Tyr Arg Asn Asn Gln Arg Pro Ser Gly Val Pro
            50                  55                  60

Asp Arg Phe Ser Gly Ser Lys Ser Gly Thr Ser Ala Ser Leu Ala
            65                  70                  75

Ile Ser Gly Leu Arg Ser Glu Asp Glu Ala Asp Tyr Tyr Cys Gln
```

-continued

```
                              80                    85                    90
Ser Tyr Asp Asn Ser Leu Asn Gly Tyr Val Phe Gly Gly Thr
                  95                   100                   105
Gln Leu Thr Val Leu Gly
              110
```

(2) INFORMATION FOR SEQ ID NO:22:

(i) SEQUENCE CHARACTERISTICS:
        (A) LENGTH: 119 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
            fUSE5 fusion phage construct
        (D) CLONE: G57

(ix) FEATURE:
        (A) NAME/KEY: heavy chain (xi) SEQUENCE DESCRIPTION: SEQ ID NO:22:

```
Gln Val Asn Leu Arg Glu Ser Gly Gly Gly Leu Val Lys Pro Gly
                 5                    10                    15
Gly Ser Leu Arg Leu Ser Cys Ala Ala Ser Gly Phe Thr Phe Ser
                 20                   25                    30
Asp Tyr Tyr Met Ser Trp Ile Arg Gln Ala Pro Gly Lys Gly Leu
                 35                   40                    45
Glu Trp Val Ser Ala Ile Ser Gly Ser Gly Gly Ser Thr Tyr Tyr
                 50                   55                    60
Thr Asp Ser Val Lys Gly Arg Phe Thr Ile Ser Arg Asp Asn Ser
                 65                   70                    75
Lys Asn Thr Leu Tyr Leu Gln Asn Ser Leu Arg Ala Glu Asp Thr
                 80                   85                    90
Ala Ile Tyr Tyr Cys Ala Lys Glu Met Asn Tyr Phe Ser His Ala
                 95                  100                   105
Met Asp Val Trp Gly Gln Gly Thr Pro Val Thr Val Ser Ser
              110                   115
```

(2) INFORMATION FOR SEQ ID NO:23:

(i) SEQUENCE CHARACTERISTICS:
        (A) LENGTH: 111 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
            fUSE5 fusion phage construct (D) CLONE: G57

(ix) FEATURE:
(A) NAME/KEY: light chain
(D) OTHER INFORMATION: Xaa in position 6 is His or Gln (xi) SEQUENCE DESCRIPTION: SEQ ID NO:23:

```
Gln Ser Val Leu Thr Xaa Pro Pro Ser Ala Ser Gly Thr Pro Gly
                 5                  10                  15

Gln Arg Val Thr Ile Ser Cys Ser Gly Ser Ser Ser Asn Ile Gly
                20                  25                  30

Ser Asn Tyr Val Tyr Trp Tyr Gln Gln Leu Pro Gly Thr Ala Pro
                35                  40                  45

Lys Leu Leu Ile Tyr Arg Asn Asn Gln Arg Pro Ser Gly Val Pro
                50                  55                  60

Asp Arg Phe Ser Gly Ser Lys Ser Gly Thr Ser Ala Ser Leu Ala
                65                  70                  75

Ile Ser Gly Leu Arg Ser Glu Asp Glu Ala Asp Tyr Tyr Cys Ala
                80                  85                  90

Ser Trp Asp Asp Ser Leu Arg Gly Trp Val Phe Gly Gly Gly Thr
                95                 100                 105

Gln Leu Thr Val Leu Ser
                110
```

(2) INFORMATION FOR SEQ ID NO:24:

(i) SEQUENCE CHARACTERISTICS:
(A) LENGTH: 118 residues
(B) TYPE: amino acid
(C) STRANDEDNESS: single
(D) TOPOLOGY: linear (ii) MOLECULE TYPE:
(A) DESCRIPTION: polypeptide (vi) ORIGINAL SOURCE:
(A) ORGANISM: Homo sapiens (melanoma patient immunized with autologous tumor cells)
(B) INDIVIDUAL ISOLATE: peripheral blood lymphocytes (vii) IMMEDIATE SOURCE:
(A) LIBRARY: DM414 scFv antibodies obtained from fUSE5 fusion phage construct
(D) CLONE: D33

(ix) FEATURE:
(A) NAME/KEY: heavy chain
(D) OTHER INFORMATION: Xaa in position 81 is Leu or Thr (xi) SEQUENCE DESCRIPTION: SEQ ID NO:24:

```
Glu Val Gln Leu Met Glu Ser Gly Ala Glu Val Lys Lys Pro Gly
                 5                  10                  15

Ala Ser Val Lys Ile Ser Cys Cys Ser Gly His Pro Phe Thr Asn
                20                  25                  30

His Trp Phe His Trp Val Arg Gln Ala Pro Gly Gln Gly Leu Glu
                35                  40                  45

Trp Met Gly Trp Val Ser Pro Asn Thr Gly Ala Thr Lys Thr Ala
                50                  55                  60

Glu Met Phe Gln Gly Arg Val Thr Asn Thr Trp Asp Thr Ser Ile
                65                  70                  75

Xaa Thr Ala Tyr Met Gly Leu Arg Ser Leu Thr Ser Glu Asp Thr
                80                  85                  90
```

```
Pro Val Tyr Tyr Cys Ala Thr Ala Ala Gly Ser Ser Tyr Tyr Phe
            95                  100                 105

Gly Asn Asp Ile Trp Arg Lys Gly Ile Pro Val Thr Val
            110                 115

(2) INFORMATION FOR SEQ ID NO:25:

(i) SEQUENCE CHARACTERISTICS:
        (A) LENGTH: 113 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
            fUSE5 fusion phage construct
        (D) CLONE: D33

(ix) FEATURE:
        (A) NAME/KEY: light chain
        (D) OTHER INFORMATION: Xaa at position 47 is His or
            Gly and Xaa at position 95 is His or Gln (xi) SEQUENCE DESCRIPTION: SEQ ID NO:25:

Glu Ile Leu Met Thr Gln Ser Pro Leu Ser Leu Pro Val Thr Pro
             5                  10                  15

Gly Gln Pro Ala Ser Ile Ser Cys Arg Ser Ser Gln Thr Leu Val
            20                  25                  30

Phe Ser Asp Gly His Asn Tyr Val Asn Trp Phe Gln Gln Arg Pro
            35                  40                  45

Ala Xaa Ser Pro Arg Arg Leu Ile Tyr Glu Leu Ser Asn Arg Asp
            50                  55                  60

Pro Gly Val Pro Asp Arg Phe Ser Asp Ser Gly Ser Asp Thr Asp
            65                  70                  75

Leu Thr Leu Lys Ile Ser Arg Val Gln Ala Glu Asp Val Gly Val
            80                  85                  90

Tyr Tyr Cys Ile Xaa Gly Thr Leu Cys Pro Phe Thr Phe Gly Gly
            95                  100                 105

Gly Thr Arg Val Glu Ile Lys Arg
            110

(2) INFORMATION FOR SEQ ID NO:26:

(i) SEQUENCE CHARACTERISTICS:
        (A) LENGTH: 126 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
```

-continued

```
          fUSE5 fusion phage construct
     (D) CLONE: Z78

(ix) FEATURE:
       (A) NAME/KEY: heavy chain (xi) SEQUENCE DESCRIPTION: SEQ ID NO:26:

Gln Val Asn Leu Arg Glu Ser Gly Gly Gly Leu Val Gln Pro Trp
                  5                  10                  15

Gly Ser Leu Arg Leu Ser Cys Ser Ala Ser Gly Phe Thr Phe Ser
                 20                  25                  30

Gly His Ala Met His Trp Val Arg Gln Ala Pro Gly Lys Gly Leu
                 35                  40                  45

Glu Ser Val Ser Ala Ile Ser Gly Asn Gly Gly Ser Thr Tyr Tyr
                 50                  55                  60

Ala Asp Ser Val Lys Gly Arg Phe Thr Ile Ser Arg Asp Asn Ser
                 65                  70                  75

Leu Asn Thr Leu Tyr Leu Gln Met Ser Ser Leu Arg Ala Glu Asp
                 80                  85                  90

Thr Ala Ile Tyr Tyr Cys Ala Arg Asp Trp Tyr Pro Asp Ser Trp
                 95                 100                 105

Ser Gly Tyr Ala Val Asp Gly Leu Asp Val Trp Ala Lys Gly Thr
                110                 115                 120

Thr Val Thr Val Ser Ser
                125

(2) INFORMATION FOR SEQ ID NO:27:

(i) SEQUENCE CHARACTERISTICS:
        (A) LENGTH: 111 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
            fUSE5 fusion phage construct
        (D) CLONE: Z78

(ix) FEATURE:
        (A) NAME/KEY: light chain (xi) SEQUENCE DESCRIPTION: SEQ ID NO:27:

Gln Ser Ala Leu Thr Gln Pro Pro Ser Val Ser Glu Ala Pro Arg
                  5                  10                  15

Gln Arg Val Thr Ile Ser Cys Ser Gly Ser Ser Ser Asn Ile Gly
                 20                  25                  30

Asn Asn Ala Val Asn Trp Tyr Gln Gln Leu Pro Gly Lys Ala Pro
                 35                  40                  45

Lys Leu Leu Ile Tyr Tyr Asp Asp Leu Leu Pro Ser Gly Val Ser
                 50                  55                  60

Asp Arg Phe Ser Gly Ser Lys Ser Gly Thr Ser Ala Ser Leu Ala
                 65                  70                  75

Ile Ser Gly Leu Gln Ser Glu Asp Glu Ala Asp Tyr Tyr Cys Ala
                 80                  85                  90
```

```
Ala Trp Asp Asp Ser Leu Asn Gly Pro Val Phe Gly Gly Gly Thr
              95                 100                 105

Lys Leu Thr Val Leu Gly
             115
```

(2) INFORMATION FOR SEQ ID NO:28:

(i) SEQUENCE CHARACTERISTICS:
        (A) LENGTH: 131 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
            fUSE5 fusion phage construct
        (D) CLONE: V13

(ix) FEATURE:
        (A) NAME/KEY: heavy chain (xi) SEQUENCE DESCRIPTION: SEQ ID NO:28:

```
Glu Val Gln Leu Val Gln Ser Gly Gly Gly Leu Val Gln Pro Gly
              5                   10                  15

Gly Ser Leu Arg Leu Ser Cys Ala Ala Ser Gly Phe Thr Phe Ser
             20                   25                  30

Ser Tyr Ala Met Ser Trp Val Arg Gln Ala Pro Gly Lys Gly Leu
             35                   40                  45

Glu Trp Val Ser Ala Ile Ser Gly Ser Gly Gly Ser Thr Tyr Tyr
             50                   55                  60

Ala Asp Ser Val Lys Gly Arg Phe Thr Ile Ser Arg Asp Asn Ser
             65                   70                  75

Lys Asn Thr Leu Tyr Leu Gln Met Asn Ser Leu Arg Ala Glu Asp
             80                   85                  90

Thr Ala Val Tyr Tyr Cys Ala Lys Gly Val Ala Pro Phe Asp Tyr
             95                  100                 105

Trp Gly Gln Gly Thr Pro Val Thr Val Ser Ser Gly Gly Gly Gly
            110                  115                 120

Ser Gly Gly Gly Gly Ser Gly Gly Gly Gly Ser
            125                  130
```

(2) INFORMATION FOR SEQ ID NO:29:

(i) SEQUENCE CHARACTERISTICS:
        (A) LENGTH: 108 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:

-continued (A) LIBRARY: DM414 scFv antibodies obtained from
                fUSE5 fusion phage construct
            (D) CLONE: V13

(ix) FEATURE:
         (A) NAME/KEY: light chain (xi) SEQUENCE DESCRIPTION: SEQ ID NO:29:

Asp Ile Gln Met Thr Gln Ser Pro Ser Ser Leu Ser Ala Ser Val
                  5                  10                  15

Gly Asp Arg Val Thr Ile Thr Cys Arg Ala Ser Gln Ser Ile Ser
                 20                  25                  30

Ser Tyr Leu Asn Tyr Tyr Gln Gln Lys Pro Gly Lys Ala Pro Lys
                 35                  40                  45

Leu Leu Ile Tyr Lys Ala Ser Ser Leu Glu Ser Gly Val Pro Ser
                 50                  55                  60

Arg Phe Ser Gly Ser Gly Ser Gly Thr Glu Phe Thr Leu Thr Ile
                 65                  70                  75

Ser Ser Leu Gln Pro Asp Asp Phe Ala Thr Tyr Tyr Cys Gln Gln
                 80                  85                  90

Tyr Asn Ser Tyr Ser Arg Thr Phe Gly Gln Gly Thr Lys Leu Glu
                 95                 100                 105

Ile Lys Arg (2) INFORMATION FOR SEQ ID NO:30:

(i) SEQUENCE CHARACTERISTICS:
          (A) LENGTH: 122 residues
          (B) TYPE: amino acid
          (C) STRANDEDNESS: single
          (D) TOPOLOGY: linear (ii) MOLECULE TYPE:
          (A) DESCRIPTION: polypeptide (vi) ORIGINAL SOURCE:
          (A) ORGANISM: Homo sapiens (melanoma patient immu-
              nized with autologous tumor cells)
          (B) INDIVIDUAL ISOLATE: peripheral blood lymphocytes (vii) IMMEDIATE SOURCE:
          (A) LIBRARY: DM414 scFv antibodies obtained from
              fUSE5 fusion phage construct
          (D) CLONE: V73

(ix) FEATURE:
          (A) NAME/KEY: heavy chain (xi) SEQUENCE DESCRIPTION: SEQ ID NO:30:

Gln Val Gln Leu Val Gln Ser Gly Ser Arg Gly Val Lys Xaa Arg
                  5                  10                  15

Gly Val Ser Xaa Ile Ser Cys Lys Gly Ser Gly Tyr Thr Phe Thr
                 20                  25                  30

Ser Tyr Trp Ile Gly Trp Val Arg Gln Ile Pro Gly Lys Gly Leu
                 35                  40                  45

Glu Trp Met Gly Ile Ile Tyr Pro Gly Asp Ser Asp Thr Arg Tyr
                 50                  55                  60

Arg Pro Ser Phe Gln Gly Gln Val Thr Ile Ser Ala Asp Lys Ser
                 65                  70                  75

Ile Ser Thr Ala Tyr Leu Gln Trp Ser Ser Leu Lys Ala Ser Asp
                 80                  85                  90

Thr Ala Met Tyr Tyr Cys Ala Arg Leu Thr Val Asp Asp Tyr Gly
                 95                 100                 105

```
Gly Asn Thr Pro Asp Tyr Trp Gly Gln Gly Thr Thr Val Thr Val
                110                 115                 120

Ser Ser (2) INFORMATION FOR SEQ ID NO:31:

(i) SEQUENCE CHARACTERISTICS:
        (A) LENGTH: 112 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
            fUSE5 fusion phage construct
        (D) CLONE: V73

(ix) FEATURE:
        (A) NAME/KEY: light chain (xi) SEQUENCE DESCRIPTION: SEQ ID NO:31:

Gln Ser Ala Leu Thr Gln Pro Pro Ser Val Ser Ala Ala Pro Gly
                 5                  10                  15

Gln Lys Val Thr Xaa Ile Ser Cys Ser Gly Ser Ser Ser Asn Ile
                20                  25                  30

Gly Asn Asn Tyr Val Ser Trp Tyr Gln Gln Leu Pro Gly Thr Ala
                35                  40                  45

Pro Lys Leu Leu Ile Tyr Glu Asn Asn Lys Arg Pro Ser Gly Ile
                50                  55                  60

Pro Asp Arg Phe Ser Gly Ser Lys Ser Gly Thr Ser Ala Thr Leu
                65                  70                  75

Gly Ile Thr Gly Leu Gln Thr Gly Asp Glu Ala Asp Tyr Tyr Cys
                80                  85                  90

Gly Thr Trp Asp Ser Ser Leu Ser Ala Glu Val Phe Gly Thr Gly
                95                 100                 105

Thr Gln Leu Thr Val Leu Gly
                110

(2) INFORMATION FOR SEQ ID NO:32:

(i) SEQUENCE CHARACTERISTICS:
        (A) LENGTH: 140 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
            fUSE5 fusion phage construct
        (D) CLONE: V86
```

(ix) FEATURE:
              (A) NAME/KEY: heavy chain and linker (xi) SEQUENCE DESCRIPTION: SEQ ID NO:32:

Gln Val Gln Leu Val Gln Ser Gly Gly Gly Leu Val Gln Pro Gly
                  5                  10                  15

Gly Ser Leu Arg Leu Ser Cys Ala Ala Ser Gly Phe Thr Phe Ser
             20                  25                  30

Ser Tyr Ala Met Ser Trp Val Arg Gln Ala Pro Gly Lys Gly Leu
             35                  40                  45

Glu Trp Val Ala Ala Ile Ser Gly Ser Gly Gly Ser Thr Tyr Tyr
             50                  55                  60

Ala Asp Ser Val Lys Gly Arg Phe Thr Ile Ser Arg Asp Asn Ser
             65                  70                  75

Lys Asn Thr Leu Tyr Leu Gln Met Asn Ser Leu Arg Ala Glu Asp
             80                  85                  90

Thr Ala Val Tyr Tyr Cys Ala Arg Gly Trp Gly Leu Arg Gly Glu
             95                 100                 105

Glu Gly Asp Tyr Tyr Met Asp Val Trp Gly Lys Gly Thr Met Val
            110                 115                 120

Thr Val Ser Ser Gly Gly Gly Ser Gly Gly Gly Gly Ser Gly
            125                 130                 135

Gly Gly Gly Ser Ser
            140

(2) INFORMATION FOR SEQ ID NO:33:

(i) SEQUENCE CHARACTERISTICS:
         (A) LENGTH: 24 residues
         (B) TYPE: amino acid
         (C) STRANDEDNESS: single
         (D) TOPOLOGY: linear (ii) MOLECULE TYPE:
         (A) DESCRIPTION: polypeptide (vi) ORIGINAL SOURCE:
         (A) ORGANISM: Homo sapiens (melanoma patient immu-
             nized with autologous tumor cells)
         (B) INDIVIDUAL ISOLATE: peripheral blood lymphocytes (vii) IMMEDIATE SOURCE:
         (A) LIBRARY: DM414 scFv antibodies obtained from
             fUSE5 fusion phage construct
         (D) CLONE: V86

(ix) FEATURE:
         (A) NAME/KEY: light chain (xi) SEQUENCE DESCRIPTION: SEQ ID NO:33:

Ser Tyr Glu Leu Thr Gln Glu Pro Arg Gly Gly Gly Thr Gln Leu
                  5                  10                  15

Thr Val Leu Gly Gly Ala Ala Gly Ala
             20

(2) INFORMATION FOR SEQ ID NO:34:

(i) SEQUENCE CHARACTERISTICS:
         (A) LENGTH: 119 residues
         (B) TYPE: amino acid
         (C) STRANDEDNESS: single
         (D) TOPOLOGY: linear (ii) MOLECULE TYPE:
         (A) DESCRIPTION: polypeptide

```
        (vi) ORIGINAL SOURCE:
              (A) ORGANISM: Homo sapiens (melanoma patient immu-
                    nized with autologous tumor cells)
              (B) INDIVIDUAL ISOLATE: peripheral blood lymphocytes (vii) IMMEDIATE SOURCE:
              (A) LIBRARY: DM414 scFv antibodies obtained from
                    fUSE5 fusion phage construct
              (D) CLONE: V373

(ix) FEATURE:
              (A) NAME/KEY: heavy chain
              (D) OTHER INFORMATION: Xaa at position 3 is Gln or
                    Xaa and Xaa at position 19 is Xaa or Ser (xi) SEQUENCE DESCRIPTION: SEQ ID NO:34:

Glu Val Xaa Xaa Xaa Xaa Xaa Xaa Xaa Xaa Xaa Xaa Xaa Xaa Xaa
                  5                  10                  15

Xaa Xaa Xaa Xaa Cys Lys Ala Ser Gly Tyr Thr Phe Thr Ser Ser
             20                  25                  30

Tyr Ile His Trp Val Arg Gln Ala Pro Gly Gln Gly Leu Glu Trp
             35                  40                  45

Met Gly Val Ile Asn Pro Ser Gly Gly Asn Thr Ile Tyr Ala Arg
             50                  55                  60

Asn Phe Gln Gly Arg Val Thr Met Thr Arg Asp Thr Ser Thr Ser
             65                  70                  75

Thr Val Tyr Met Glu Leu Ser Ser Leu Arg Phe Glu Asp Thr Ala
             80                  85                  90

Val Tyr Tyr Cys Ala Arg Asp Arg Arg Tyr Cys Ser Gly Gly Ser
             95                 100                 105

Cys Tyr Ala Glu Val Val Tyr Trp Gly Gln Gly Thr Thr Val
            110                 115

(2) INFORMATION FOR SEQ ID NO:35:

(i) SEQUENCE CHARACTERISTICS:
              (A) LENGTH: 111 residues
              (B) TYPE: amino acid
              (C) STRANDEDNESS: single
              (D) TOPOLOGY: linear (ii) MOLECULE TYPE:
              (A) DESCRIPTION: polypeptide (vi) ORIGINAL SOURCE:
              (A) ORGANISM: Homo sapiens (melanoma patient immu-
                    nized with autologous tumor cells)
              (B) INDIVIDUAL ISOLATE: peripheral blood lymphocytes (vii) IMMEDIATE SOURCE:
              (A) LIBRARY: DM414 scFv antibodies obtained from
                    fUSE5 fusion phage construct
              (D) CLONE: V373

(ix) FEATURE:
              (A) NAME/KEY: light chain (xi) SEQUENCE DESCRIPTION: SEQ ID NO:35:

Gln Ser Ala Leu Thr Gln Pro Pro Ser Val Ser Ala Ala Pro Gly
                  5                  10                  15

Gln Lys Val Thr Ile Ser Cys Ser Gly Ser Ser Ser Asn Ile Gly
             20                  25                  30

Asn Asn Tyr Val Ser Trp Tyr Gln Arg Leu Pro Gly Thr Ala Pro
             35                  40                  45

Lys Leu Leu Ile Tyr Glu Asn Asn Lys Arg Pro Ser Gly Ile Pro
```

-continued

```
                50                   55                   60
Asp Arg Phe Ser Gly Ser Lys Ser Gly Thr Ser Ala Thr Leu Ala
                    65                   70                   75

Ile Thr Gly Leu Gln Ala Glu Asp Glu Ala Gly Tyr Tyr Cys Gln
                    80                   85                   90

Ser Tyr Asp Ser Ser Leu Ser Gly Tyr Val Phe Gly Thr Gly Thr
                    95                  100                  105

Lys Leu Thr Val Leu Gly
                110
```

(2) INFORMATION FOR SEQ ID NO:36:

(i) SEQUENCE CHARACTERISTICS:
        (A) LENGTH: 116 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immu-
            nized with autologous tumor cells)
        (B) INDIVIDUAL ISOLATE: peripheral blood lymphocytes (vii) IMMEDIATE SOURCE:
        (A) LIBRARY: DM414 scFv antibodies obtained from
            fUSE5 fusion phage construct
        (D) CLONE: V474

(ix) FEATURE:
        (A) NAME/KEY: heavy chain (xi) SEQUENCE DESCRIPTION: SEQ ID NO:36:

```
Glu Val Gln Leu Val Gln Ser Gly Gly Gly Leu Val Gln Pro Gly
                 5                   10                   15

Gly Ser Leu Arg Leu Ser Cys Ala Ala Ser Gly Phe Thr Phe Ser
                    20                   25                   30

Ser Tyr Thr Met Ser Trp Val Arg Gln Ala Pro Gly Lys Gly Leu
                    35                   40                   45

Glu Trp Val Ser Ala Ile Ser Gly Ser Gly Gly Ser Thr Tyr Tyr
                    50                   55                   60

Ala Asp Ser Val Lys Gly Arg Phe Thr Ile Ser Arg Asp Asn Ser
                    65                   70                   75

Lys Asn Thr Arg Tyr Leu Gln Met Asn Ser Leu Arg Ala Glu Asp
                    80                   85                   90

Thr Ala Val Tyr Tyr Cys Ala Lys Gly Val Ala Pro Phe Asp Tyr
                    95                  100                  105

Trp Gly Glu Gly Thr Pro Val Thr Val Ser Ser
                110                  115
```

(2) INFORMATION FOR SEQ ID NO:37:

(i) SEQUENCE CHARACTERISTICS:
        (A) LENGTH: 108 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient immunized with autologous tumor cells)
            (B) INDIVIDUAL ISOLATE: peripheral blood lymphocytes (vii) IMMEDIATE SOURCE:
            (A) LIBRARY: DM414 scFv antibodies obtained from
                fUSE5 fusion phage construct
            (D) CLONE: V474

(ix) FEATURE:
            (A) NAME/KEY: light chain (xi) SEQUENCE DESCRIPTION: SEQ ID NO:37:

Asp Ile Gln Met Thr Gln Ser Pro Ser Ser Leu Ser Ala Ser Val
                  5                  10                  15

Gly Asp Arg Val Thr Ile Thr Cys Arg Ala Ser Gln Ser Ile Ser
                 20                  25                  30

Ser Tyr Leu Asn Trp Tyr Gln Gln Lys Glu Gly Lys Ala Pro Lys
                 35                  40                  45

Leu Leu Ile Tyr Lys Ala Ser Ser Leu Glu Ser Gly Val Pro Ser
                 50                  55                  60

Arg Phe Ser Gly Ser Gly Ser Gly Thr Glu Phe Thr Leu Thr Ile
                 65                  70                  75

Ser Ser Leu Gln Pro Asp Asp Phe Ala Thr Tyr Tyr Cys Gln Gln
                 80                  85                  90

Tyr Asn Ser Ser Arg Thr Phe Gly Gln Gly Thr Lys Leu Gly
                 95                 100                 105

Ile Lys Arg (2) INFORMATION FOR SEQ ID NO:38:

(i) SEQUENCE CHARACTERISTICS:
            (A) LENGTH: 123 residues
            (B) TYPE: amino acid
            (C) STRANDEDNESS: single
            (D) TOPOLOGY: linear (ii) MOLECULE TYPE:
            (A) DESCRIPTION: polypeptide (vi) ORIGINAL SOURCE:
            (A) ORGANISM: Homo sapiens (melanoma patient
                immunized with autologous tumor cells)
            (B) INDIVIDUAL ISOLATE: peripheral blood lympho-
                cytes (vii) IMMEDIATE SOURCE:
            (A) LIBRARY: DM414 scFv antibodies obtained from
                fUSE5 fusion phage construct
            (D) CLONE: V575

(ix) FEATURE:
            (A) NAME/KEY: heavy chain (xi) SEQUENCE DESCRIPTION: SEQ ID NO:38:

Gln Val Gln Leu Val Glu Ser Gly Gly Gly Val Val Gln Pro Gly
                  5                  10                  15

Arg Ser Leu Arg Leu Ser Cys Ala Ala Ser Gly Phe Thr Phe Ser
                 20                  25                  30

Ser Tyr Ala Met His Trp Val Arg Gln Ala Pro Gly Lys Gly Leu
                 35                  40                  45

Glu Trp Val Ala Val Ile Ser Tyr Asp Gly Ser Asn Lys Tyr Tyr
                 50                  55                  60

Ala Asp Ser VAl Lys Gly Arg Phe Thr Ile Ser Arg Asp Asn Ser
                 65                  70                  75

```
Lys Lys Asn Thr Leu Tyr Leu Gln Met Asn Ser Leu Arg Ala Glu
                80                  85                  90

Asp Thr Ala Val Tyr Tyr Cys Ala Arg Gly Phe Pro Tyr Gly Gly
                95                 100                 105

Asn Ser Asp Tyr Gly Met Asp Val Trp Asp His Gly Thr Gln Val
               110                 115                 120

Thr Val Ser
```

(2) INFORMATION FOR SEQ ID NO:39:

(i) SEQUENCE CHARACTERISTICS:
        (A) LENGTH: 17 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:39:

TGATTTTCTG TATGAGG                                          17

(2) INFORMATION FOR SEQ ID NO:40:

(i) SEQUENCE CHARACTERISTICS:
        (A) LENGTH: 21 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:40:

ACCCGACCCA CCACCGCCCG A                                21

(2) INFORMATION FOR SEQ ID NO:41:

(i) SEQUENCE CHARACTERISTICS:
        (A) LENGTH: 24 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:41:

GTCCACCTTG GTGTTGCTGG GCTT                            24

(2) INFORMATION FOR SEQ ID NO:42:

(i) SEQUENCE CHARACTERISTICS:
        (A) LENGTH: 50 residues
        (B) TYPE: nucleic acid
        (C) STRANDEDNESS: single
        (D) TOPOLOGY: linear (ii) MOLECULE TYPE: DNA
        (A) DESCRIPTION: primer used in constructs (xi) SEQUENCE DESCRIPTION: SEQ ID NO:42:

ATGGCTCAGG GTTCGGCCGA CGTGGCCCAG GTRCAGCTGS WGSAGTCKGG        50

(2) INFORMATION FOR SEQ ID NO:43:

(i) SEQUENCE CHARACTERISTICS:

(A) LENGTH:  50 residues
        (B) TYPE: nucleic acid
        (C) STRANDEDNESS: single
        (D) TOPOLOGY: linear (ii) MOLECULE TYPE:  DNA
        (A) DESCRIPTION: primer used in constructs (xi) SEQUENCE DESCRIPTION: SEQ ID NO:43:

ATGGCTCAGG GTTCGGCCGA CGTGGCCCAG GTCAACTTAA GGGAGTCTGG                    50

(2) INFORMATION FOR SEQ ID NO:44:

(i) SEQUENCE CHARACTERISTICS:
        (A) LENGTH:  50 residues
        (B) TYPE: nucleic acid
        (C) STRANDEDNESS: single
        (D) TOPOLOGY: linear (ii) MOLECULE TYPE:  DNA
        (A) DESCRIPTION: primer used in constructs (xi) SEQUENCE DESCRIPTION: SEQ ID NO:44:

ATGGCTCAGG GTTCGGCCGA CGTGGCCGAG GTGCAGCTGK TGSAGTCTGS                    50

(2) INFORMATION FOR SEQ ID NO:45:

(i) SEQUENCE CHARACTERISTICS:
        (A) LENGTH:  60 residues
        (B) TYPE: nucleic acid
        (C) STRANDEDNESS: single
        (D) TOPOLOGY: linear (ii) MOLECULE TYPE:  DNA
        (A) DESCRIPTION: primer used in constructs (xi) SEQUENCE DESCRIPTION: SEQ ID NO:45:

ACGTTCGGCC CCAGCGGCCC CGCTACCCCC GCCTCCTGAR GAGACGGTGA                    50

CCRKKGTYCC                                                                60

(2) INFORMATION FOR SEQ ID NO:46:

(i) SEQUENCE CHARACTERISTICS:
        (A) LENGTH: 117 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient
            immunized with autologous tumor cells)
        (B) INDIVIDUAL ISOLATE: peripheral blood lympho-
            cytes (vii) IMMEDIATE SOURCE:
        (A) LIBRARY: VH antibodies obtained from fUSE5
            fusion phage construct
        (D) CLONE: C55

(ix) FEATURE:
        (A) NAME/KEY: heavy chain (xi) SEQUENCE DESCRIPTION: SEQ ID NO:46:

Glu Val Gln Leu Val Gln Ser Gly Gly Gly Leu Val Gln Pro Gly
                5                   10                  15

Gly Ser Leu Arg Leu Ser Cys Ala Ala Ser Gly Phe Thr Phe Ser
            20                  25                  30

```
Ser Tyr Ala Met Ser Trp Val Arg Gln Ala Pro Gly Lys Gly Leu
                35                  40                  45

Glu Trp Val Ser Ala Ile Ser Gly Ser Gly Gly Ser Thr Tyr Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Ala Ala Val Tyr Tyr Cys Ala Thr Gly Gly Leu Leu Ser Asp
                95                 100                 105

Tyr Trp Gly Gln Gly Thr Pro Val Thr Val Ser Ser
               110                 115

(2) INFORMATION FOR SEQ ID NO:47:

(i) SEQUENCE CHARACTERISTICS:
        (A) LENGTH: 124 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient
            immunized with autologous tumor cells)
        (B) INDIVIDUAL ISOLATE: peripheral blood lympho-
            cytes (vii) IMMEDIATE SOURCE:
        (A) LIBRARY: VH antibodies obtained from fUSE5
            fusion phage construct
        (D) CLONE: E26

(ix) FEATURE:
        (A) NAME/KEY: heavy chain (xi) SEQUENCE DESCRIPTION: SEQ ID NO:47:

Gln Val Gln Leu Val Gln Ser Gly Gly Gly Leu Val Gln Pro Gly
                 5                  10                  15

Gly Ser Leu Arg Leu Ser Cys Ala Ala Ser Gly Phe Thr Phe Tyr
                20                  25                  30

Ser Tyr Ala Met Ser Trp Val Arg Gln Thr Pro Gly Lys Gly Leu
                35                  40                  45

Glu Trp Val Ser Ala Ile Gly Gly Ser Gly Val Ser Thr Tyr Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Trp Gly Leu Arg Gly Glu
                95                 100                 105

Glu Gly Asp Tyr Tyr Met Asp Val Trp Gly Lys Gly Thr Gln Val
               110                 115                 120

Thr Val Ser Ser (2) INFORMATION FOR SEQ ID NO:48:

(i) SEQUENCE CHARACTERISTICS:
        (A) LENGTH: 126 residues
        (B) TYPE: amino acid
```

(C) STRANDEDNESS: single
            (D) TOPOLOGY: linear (ii) MOLECULE TYPE:
            (A) DESCRIPTION: polypeptide (vi) ORIGINAL SOURCE:
            (A) ORGANISM: Homo sapiens (melanoma patient
                immunized with autologous tumor cells)
            (B) INDIVIDUAL ISOLATE: peripheral blood lympho-
                cytes (vii) IMMEDIATE SOURCE:
            (A) LIBRARY: VH antibodies obtained from fUSE5
                fusion phage construct
            (D) CLONE: F2

(ix) FEATURE:
            (A) NAME/KEY: heavy chain (xi) SEQUENCE DESCRIPTION: SEQ ID NO:48:

Gln Val Gln Leu Val Gln Ser Gly Gly Gly Val Val Gln Pro Gly
                 5                  10                  15

Arg Ser Leu Arg Leu Ser Cys Ala Ala Ser Gly Phe Thr Phe Ser
                20                  25                  30

Asp Cys Tyr Met Ser Trp Ile Arg Gln Ala Pro Gly Lys Gly Leu
                35                  40                  45

Glu Trp Val Ser Tyr Ile Ser Ser Ser Ser Thr Ile Tyr Tyr
                50                  55                  60

Ala Asp Ser Val Lys Gly Arg Phe Thr Ile Ser Arg Asp Asn Ala
                65                  70                  75

Lys Asn Ser Leu Tyr Leu Gln Met Asn Ser Leu Arg Asp Glu Asp
                80                  85                  90

Thr Ala Val Tyr Tyr Cys Ala Arg Asp Ser Ser Gly Ser Tyr Ser
                95                 100                 105

Glu Arg Asp Tyr Tyr Tyr Gly Met Asp Val Trp Gly Gln Gly Thr
               110                 115                 120

Pro Val Thr Val Ser Ser
               125

(2) INFORMATION FOR SEQ ID NO:49:

(i) SEQUENCE CHARACTERISTICS:
            (A) LENGTH: 112 residues
            (B) TYPE: amino acid
            (C) STRANDEDNESS: single
            (D) TOPOLOGY: linear (ii) MOLECULE TYPE:
            (A) DESCRIPTION: polypeptide (vi) ORIGINAL SOURCE:
            (A) ORGANISM: Homo sapiens (melanoma patient
                immunized with autologous tumor cells)
            (B) INDIVIDUAL ISOLATE: peripheral blood lympho-
                cytes (vii) IMMEDIATE SOURCE:
            (A) LIBRARY: VH antibodies obtained from fUSE5
                fusion phage construct
            (D) CLONE: F2

(ix) FEATURE:
            (A) NAME/KEY: light chain (xi) SEQUENCE DESCRIPTION: SEQ ID NO:49:

Gln Ser Ala Leu Thr Glu Pro Pro Ser Val Ser Gly Ala Pro Gly
                 5                  10                  15

```
Gln Arg Val Thr Ile Ser Cys Thr Gly Ser Thr Ser Asn Ile Gly
                20                  25                  30

Ala Gly Tyr Asp Val Arg Trp Tyr Gln His Leu Pro Gly Thr Val
                35                  40                  45

Pro Lys Leu Leu Ile Tyr Thr Asn Ser Ile Arg Pro Ser Gly Val
                50                  55                  60

Pro Asp Arg Phe Ser Gly Ser Lys Ser Gly Thr Ser Ala Ser Leu
                65                  70                  75

Thr Ile Asp Gly Leu Gln Ser Glu Asp Glu Ala Asp Tyr Tyr Cys
                80                  85                  90

Ala Thr Trp Asp Asp Arg Leu Asp Gly Tyr Val Phe Ala Thr Gly
                95                 100                 105

Thr Gln Leu Thr Val Leu Gly
               110

(2) INFORMATION FOR SEQ ID NO:50:

(i) SEQUENCE CHARACTERISTICS:
        (A) LENGTH: 119 residues
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Homo sapiens (melanoma patient
            immunized with autologous tumor cells)
        (B) INDIVIDUAL ISOLATE: peripheral blood lympho-
            cytes (vii) IMMEDIATE SOURCE:
        (A) LIBRARY: VH antibodies obtained from fUSE5
            fusion phage construct
        (D) CLONE: 2-71

(ix) FEATURE:
        (A) NAME/KEY: heavy chain (xi) SEQUENCE DESCRIPTION: SEQ ID NO:50:

Ala Ala Gly Gly Ala Val Gly Gly Leu Glu Val Lys Lys Pro Gly
                 5                  10                  15

Ser Ser Val Lys Val Ser Cys Lys Ala Ser Gly Gly Thr Phe Ser
                20                  25                  30

Ser Tyr Ala Ile Ser Trp Val Arg Gln Ala Pro Gly Gln Gly Leu
                35                  40                  45

Glu Trp Met Gly Gly Ile Ile Pro Ile Phe Gly Thr Ala Asn Tyr
                50                  55                  60

Ala Gln Lys Phe Gln Gly Arg Val Thr Ile Thr Ala Asp Lys Ser
                65                  70                  75

Thr Ser Thr Ala Tyr Met Glu Leu Ser Ser Leu Arg Ser Glu Asp
                80                  85                  90

Thr Ala Val Tyr Tyr Cys Ala Arg Gly Gly Arg Tyr Asp Ala
                95                 100                 105

Phe Asp Ile Trp Gly Gln Gly Thr Leu Val Thr Val Ser Ser
               110                 115

(2) INFORMATION FOR SEQ ID NO:51:

(i) SEQUENCE CHARACTERISTICS:
        (A) LENGTH: 124 residues
```

```
          (B) TYPE: amino acid
          (C) STRANDEDNESS: single
          (D) TOPOLOGY: linear (ii) MOLECULE TYPE:
          (A) DESCRIPTION: polypeptide (vi) ORIGINAL SOURCE:
          (A) ORGANISM: Homo sapiens (melanoma patient
                immunized with autologous tumor cells)
          (B) INDIVIDUAL ISOLATE: peripheral blood lympho-
                cytes (vii) IMMEDIATE SOURCE:
          (A) LIBRARY: VH antibodies obtained from fUSE5
                fusion phage construct
          (D) CLONE: E-13

(ix) FEATURE:
          (A) NAME/KEY: heavy chain (xi) SEQUENCE DESCRIPTION: SEQ ID NO:51:

Glu Val Gln Leu Leu Glu Ser Ala Gly Gly Leu Val Gln Pro Gly
                  5                  10                  15

Gly Ser Leu Arg Leu Ser Cys Ala Ala Ser Gly Phe Thr Phe Ser
                 20                  25                  30

Ser Tyr Ala Met Ser Trp Val Arg Gln Ala Pro Gly Lys Gly Leu
                 35                  40                  45

Glu Trp Val Ser Ala Ile Ser Gly Ser Gly Gly Ser Thr Tyr Tyr
                 50                  55                  60

Ala Asp Ser Val Lys Gly Arg Phe Thr Ile Ser Arg Asp Asn Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Gly Trp Gly Leu Arg Gly Glu
                 95                 100                 105

Glu Gly Asp Tyr Tyr Val Asp Val Trp Gly Lys Gly Thr Lys Val
                110                 115                 120

Thr Val Leu Gly
```

HUMAN MONOCLONAL ANTI-TUMOR ANTIBODIES

RELATED APPLICATION DATA

This is a 371 of PCT/IB96/01032 filed Jun. 28, 1996 which is a of U.S. application Ser. No. 08/497,647 filed Jun. 30, 1995 now abandoned.

TECHNICAL FIELD OF THE INVENTION

This invention relates to the preparation of human monoclonal anti-tumor scFv and $V_H$ antibodies derived from the antibody repertoires of cancer patients.

Among the various strategies for the treatment and prevention of cancer, immunotherapy has long occupied a central position. Although the clinical results have not lived up to early expectations, the remarkable recent advances in our understanding of the immune system and in our ability to manipulate it has refocused interest in cancer immunology. Antibodies and T-cells are extremely selective agents for targeting specific cell types. Human monoclonal antibodies provide the further advantage of weak immunogenicity in humans.

BACKGROUND OF THE INVENTION

A major focus of cancer immunology is on the isolation of antibodies that react selectively with human tumor cells, since the antibodies could have important applications for targeting diagnostic and therapeutic agents to tumors and for identifying tumorigenic antigens. The established approach has been to generate large panels of monoclonal antibodies from mice immunized with human tumor cells, and to screen the antibodies for reactivity against the tumor. Despite the enormous effort expended on this approach, few antibodies that react preferentially with human tumors, and none that react specifically with one type of tumor, have been reported.

These results are disappointing but not necessarily conclusive, because the antibodies were generated in an xenogeneic system. Human antigens are generally recognized as foreign by the murine system, and since the tumor antigens are predominately nonspecific, the murine response to human tumors will be correspondingly nonspecific.

Another approach involves generating human monoclonal antibodies from cancer patients by cloning lymphocytes transformed with Epstein-Barr virus or fused with myeloma or B-lymphoblastoid cells. However, the number of clones that can be produced with these procedures is severely limited by technical obstacles, and the antibodies isolated from the clones have shown specificities similar to those obtained with murine monoclonal antibodies.

Further attempts to isolate more specific antibodies will require improved methods of generating and selecting antibodies against human tumors. Two recent developments may be useful in this regard. One involves immunizing cancer patients with autologous tumor cells which have been genetically modified to boost the immunogenicity of the cells (Dranoff, G. & Mulligan, R. C. (1995) *Adv. Immunol.* 58, 417–454). Although there is an extensive normal human repertoire of anti-self antibodies (Griffiths A. D., et al., (1993) *EMBO J* 12, 725–734), indicating that the human immune system can respond toself antigens, the humoral response of the immunized cancer patients might be directed preferentially against any non-self antigens expressed by the autologous or allogeneic tumor cells. Numerous such immunization trials are in progress with melanoma, renal and colon carcinoma, neuroblastoma and breast cancer patients, and others are planned.

The other new development is the introduction of methods for synthesizing virtually the entire repertoire of any person's antibody genes, and for expressing the encoded Fab or scFv antibody fragments on the surface of a fusion-phage vector (see, for example, Marks, J., et al., (1991) *J. Mol. Biol.* 222, 581–597). The resulting fusion-phage antibody library can be panned to select and clone rare antibodies on the basis of their binding specificities.

SUMMARY OF THE INVENTION

One object of the invention is to provide a new procedure for isolating human monoclonal anti-tumor scFv and $V_H$ antibodies from cancer patients. The use of $V_H$ as well as scFv antibodies is an important innovative modification of the procedure.

It is a further and more specific object of the invention to provide human monoclonal anti-tumor antibodies that are specific against one or more types of tumors, or a specific tumor lineage, and human monoclonal anti-endothelial cell antibodies that can target the tumor vasculature.

These and other objects are achieved by the present invention, which provides a process for isolating human monoclonal scFv and $V_H$ antibodies by constructing a fusion phage library from a cancer patient's peripheral blood lymphocytes or lymph node tissue containing metastatic tumor tissue; selecting for anti-tumor and anti-endothelial antibodies in the phage library in a binding assay with cultured tumor, endothelial or other cell types, or with purified antigens; removing antibodies that also bind to normal cells by absorption against normal human cells; cloning the phage; assaying the specificity of the cloned phage in a binding assay with at least two types of cultured normal cells; and further testing the specificity of cloned phage that do not bind to the cultured normal cells in a further binding assay to cultured tumor cells.

In some preferred processes, the cancer patients are first immunized to enhance their immune response against the tumor cells prior to using the peripheral blood lymphocytes for construction of the fusion phage library. In some embodiments, this involves immunization with cultured autologous or allogeneic tumor cells; particularly preferred are immunizations with cultured autologous or allogeneic tumor cells transduced with a cytokine such as γ-interferon, interleukin-4, GM-CSF, or the like. In other embodiments, libraries are constructed from a cancer patient's lymph node tissue containing metastatic tumor tissue.

Fusion phage antibody libraries typically display single-chain Fv (scFv) antibody fragments. Diverse libraries of immunoglobulin heavy ($V_H$) and light ($V_\kappa$ and $V_\lambda$) chain variable (V) genes are prepared from lymphocytes by polymerase chain (PCR) amplification. Genes encoding scFv fragments are made by randomly combining heavy and light V-chains using PCR, and the combinational library cloned for antibody display on the surface of a phage. *Escherichia coli* phage such as fUSE5 are employed in some embodiments.

In one embodiment, the fusion phage are preferably screened at least two or three times against cultured human tumor cells to enrich for anti-tumor antibodies, and then absorbed against cultured normal human cells to remove antibodies that also bind to normal cells. The selected phage are then cloned and those that do not bind to at least two normal human cell types are chosen for further characterization in a series of incubations with various types of cultured human tumor cells. ELISAs are typically employed as binding assays.

In preferred embodiments, the incubation with tumor cell cultures comprises a series of incubations with at least five different tumor cell cultures, including cultures of the original tumor type, cultures of a related tumor type having the same lineage, and cultures of unrelated tumor types. This procedure identifies antibodies that are specific to the original tumor, to tumors of the same lineage, or to more than one type of tumor. Such antibodies are of use for both diagnostic and therapeutic purposes, and as probes for isolating the cognate tumor antigens.

In one embodiment, scFv and $V_H$ antibody fusion phage libraries of melanoma patients immunized with gene-modified autologous or allogeneic melanoma cells or lymph nodes containing metastatic tissue obtained from the patients are screened for binding to the autologous or allogeneic cells in preferably at least two rounds of selection. Antibodies that bind after both rounds are absorbed against human fibroblast cells, and the remaining phage are cloned. These phage are first tested by enzyme-linked immunosorbent assay (ELISA) for binding to two normal human cell types such as endothelial cells and fibroblasts. Antibodies that fail to bind to the normal cells are further tested by ELISA for binding to a panel of tumor cells, including several different melanomas and other tumors, and normal melanocytes. Further tests are also performed with normal and tumor tissue sections. Tumor-specific, melanocytic lineage-specific, and melanoma-specific human monoclonal single-chain Fv and $V_H$ antibodies are identified and sequenced.

The invention further provides single-chain Fv and $V_H$ antibodies prepared according to the process of the invention, including specific antibodies of defined sequences given hereinafter. Related thereto are immunoconjugates synthesized from scFv or $V_H$ antibodies identified by processes of the invention conjugated to an effector domain that can induce a cytotoxic effect against the tumor. Also encompassed are tumor antigens that bind to an antibody produced according to processes of the invention.

DETAILED DESCRIPTION OF THE INVENTION

This invention is based upon the finding that single-chain Fv and $V_H$ antibody genes encoding melanoma-specific, tumor-specific, and melanocytic lineage-specific human monoclonal antibodies can be synthesized and cloned from immunized cancer patients.

In the practice of the invention, fusion phage libraries are constructed from the peripheral blood lymphocytes (PBL) or lymph nodes of a cancer patient. By way of illustration and because it is the preferred embodiment, the patients described in the Examples section are human, but the process is equally applicable to veterinary patients. The patient is preferably immunized to enhance the immune response to the tumor so that a humoral anti-tumor titer is observed in one embodiment. Any method that enhances the immunologic response to the tumor may be employed, such as genetic manipulation of tumor cells followed by inoculation of the patient with the modified cells, leading to protection against subsequent challenge of wild-type tumor. A number of such methods have been suggested and are described by Dranoff and Mulligan, cited above, including, but not limited to, systemic administration of recombinant cytokines, tumor antigen-based vaccination schemes, and engineering of tumor cells to express cytokines such as γ-interferon, GM-CSF, an interleukin such as IL-2, IL-4, and the like, using a retroviral or adeno-associated viral vector. In one embodiment, patients are immunized with gene-modified autologous or allogeneic melanoma cells that have been transfected with human γ-interferon. Other embodiments employ a patient's lymph node tissue containing metastatic tumor tissue. In these embodiments, the patient may or may not be immunized.

Virtually the entire repertoire of a person's antibody genes may be sythesized from the peripheral blood lymphocytes using polymerase chain reaction (PCR) technology. (See, for example, Winter, G., and Milstein, C., (1991) Nature 349, 293–199.) As used herein, "antibody" includes complete antibodies and antibody fragments that bind to antigen such as Fab fragments, scFv fragments containing heavy and light chains linked by peptides, and $V_H$ fragments. The term "anti-tumor antibodies" refers to antibodies to the tumors themselves and tumor-related products and structures, and specifically includes vascular structures supporting tumor growth, proliferation and metastasis. Thus, this invention provides in some instances anti-tumor antibodies to the cancer per se and anti-tumor vasculature antibodies.

In the practice of the invention, antibody libraries are typically prepared by first synthesizing cDNAs from poly $(A)^+$ RNA isolated from the patient's lymphocytes using random hexamers and oligo dT primers supplied by commercially available kits. Genes encoding the variable region heavy chain ($V_H$) for IgG and IgM heavy chains, the κ and λ light chain, and peptide linkers joining the 3'-end of the heavy-chains with the 5' end of the light chain, are synthesized using PCR. The $V_H$-linker-$V_L$ scFv and $V_H$ cDNAs are then prepared using PCR. As used herein, the term "cDNA" specifically includes cDNA prepared as outlined above or similar means, and closely related or homologous DNA, particularly DNA that hybridizes under stringent conditions to cDNA so prepared.

The antibody cDNAs so produced are then ligated into the phage display vector such as fUSE5 for *Escherichia coli* described by Scott, J. K. & Smith, G. P. (1990) *Science* 249, 386–390. These typically are filamentous phage that display V-gene libraries on the phage surface. Procedures for the construction of fusion phage antibody libraries are given in Marks, et al., cited above, and in the Examples section below.

Fusion phage libraries expressing scFv and $V_H$ antibodies are screened for binding to the respective tumors in what is described in the literature as a "panning" step. For the practice of the invention, this involves binding of the phage with live or fixed cultured tumor cells to select for phage that bind to the cells, and typically involves incubation of the phage with the tumor cells for a time under conditions sufficient to obtain binding of at least a portion of the phage to the cells. In preferred embodiments, the screen includes at least two or three consecutive pannings of phage against cultures of the same tumor type. Where an autologous or allogeneic tumor cell line was used to immunize a patient, this culture is preferred, but other lines of the same tumor can be substituted.

Preferred procedures for obtaining anti-melanoma antibodies then include extensive absorption against melanocytes to increase the chances of finding antibodies specific to the tumor. For the preparation of other tumor antibodies, the step includes extensive absorption against the normal progenitor cell of the particular tumor if these are available, or alternatively another normal cell type.

Following panning and absorption, the selected phage are then cloned and the specificities of the cloned phage are tested against human normal cultured cells. In preferred embodiments, to enhance the efficacy of this screening step, at least two normal cultured cell lines are employed. Any human normal cell culture may be employed in the binding assays; fibroblast and endothelial cells are employed in one embodiment. Any immunoassay that tests for binding specificity familiar to the skilled artesan may be used in this step and subsequent steps involving measures of binding with cells, such as, for example radioimmunoassays (RIAs), ELISAs, combinations of these procedures, and the like. Because of their simplicity and ease of use, ELISAs are preferred.

Cloned phage that do not bind to normal cells are then tested in binding assays with cultured human tumor cells, including lines of the same tumor type and other types. For anti-melanoma antibodies, for example, preferred panels comprise a series several, e.g., in some embodiments between five and ten, different human tumor cell cultures comprising autologous or allogeneic melanoma cells, other melanoma cells, unrelated tumor cells, and also normal melanocytes. In especially preferred embodiments, the panel includes at least one cell line from the same lineage as the tumor cell line; in an embodiment illustrating anti-melanoma antibodies in the Examples that follow, a glioma line derived from glial cells that share a common lineage with melanocytes was employed.

Any number and mixtures of cultured tumor cell lines can be used in the panel, and many are readily available from the American Type Culture Collection (A.T.C.C., 12301 Parklawn Drive, Rockville, Md. 20852) as a stock item. Examples include, but are not limited to, melanoma cells, pancreatic carcinoma cells, breast carcinoma cells, ovarian carcinoma cells, colorectal carcinoma cells, prostate carcinoma cells, gastric carcinoma cells, renal carcinoma cells, and the like given hereinafter. Examples of cloned phage bearing anti-melanoma antibodies, anti-melanocyte lineage tumor antibodies, and anti-tumor antibodies, for example, are set out below. The single-chain Fv and $V_H$ genes in the selected phage of choice are then sequenced. Examples are set out below in the next section and listed in the Sequence Listing section as SEQ ID NOs 20 to 59.

Antibody specificity is further assessed using immuno-histochemistry of cultured cells and tissue slides so that clones useful for specific diagnostic and therapeutic purposes are identified. Further improvement of the antibodies can be achieved by recombinant DNA procedures involving site-directed mutagenesis and/or variable chain exchanges, followed by panning against the original tumor cells.

This invention provides for the cloning and manufacture of human anti-tumor monoclonal antibodies either as fusion phage antibodies, or immunoconjugants synthesized from scFv or $V_H$ antibodies identified as described herein and conjugated to an effector domain that can induce a cytotoxic effect against the tumor. The cDNAs encoding the antibodies can be employed to express the antibodies in any system known to those skilled in the art, in addition to those set out herein. This invention thus encompasses additional sequences, depending upon vector construction, that facilitate expression of the cDNA in these systems, particularly on a large scale. The invention also encompasses homologous sequences, particularly those having at least about 80% sequence homology.

The anti-tumor antibodies of the invention have at least three important advantages when compared to currently available monoclonal antibodies which are generated in mice. First, since these are human antibodies, the strong immune rejection that occurs when mouse antibodies are injected into humans is avoided. Second, since the antibodies are isolated from fusion phage libraries, their affinity and specificity for a tumor cell line can be improved by genetic manipulations. Third, the antibodies can be readily conjugated to other molecules for diagnostic and therapeutic applications, and for isolating the cognate tumor antigens which could be useful as anti-cancer vaccines.

Thus, the anti-tumor monoclonal antibodies of the invention are useful in a number of applications. For diagnosis, tagged antibodies of the invention can be used to identify tumor cells in tissue slices from biopsies.

For therapy, toxin-linked antibodies of the invention target human tumor tissues (see, for example, the a recent summary by Ghetie, M. -A., and Vitetta, E. S., (1994) *Curr. Opin. Immunol.* 6, 707–714), and such linked antibodies provide immunotoxins for a large variety of tumors, including melanoma. The effectiveness of scFv and $V_H$ antibody targeting can also be enchanced using recombinant technology to increase tumor affinity of the antibody. The cytotoxicity of immunotoxins can be tested in vitro against cultured cells, and in vivo using animal models. Immunoconjugate molecules containing scFv or $V_H$ antibodies identified by processes of the invention, or homologous sequences, conjugated to an effector domain that can induce a cytotoxic effect against the tumor are thus also included in the practice of the invention. Examples of effector domains include, but are not limited to, the Fc region in human IgG or IgM, or a bacterial superantigen such as SEA.

In addition, the invention provides a way to identify antigens that react with scFv and $V_H$ antibodies by screening cDNA expression libraries such as those constructed from the tumor type of a patient with tagged antibodies. Alternatively, antigen can be isolated from a two-dimensional Western blot and partially sequenced, and a nucleic acid probe encoding that sequence used to isolate a cDNA clone. Antigen may also be isolated by immunoaffinity chromatography of a solubilized labelled melanoma cell preparation. The invention thus provides isolated tumor antigens that bind to antibodies produced according to processes of the invention.

EXAMPLES

The following examples are presented to further illustrate and explain the present invention and should not be taken as limiting in any regard.

Example 1

This example describes anti-melanoma antibodies from melanoma patients immunized with genetically modified autologous tumor cells and selection of specific antibodies from single-chain Fv fusion phage libraries. Some of the research is set out in Cai, X., and Garen, A., *Proc. Natl. Acad. Sci.*, 92:6537–6541 (1995).

Preparation of peripheral blood lymphocytes (PBL).

PBL were isolated from two melanoma patients (DM341 and DM414) of Dr. Hilliard Seigler at Duke University Medical Center. The patients had been immunized with cultured autologous tumor cells infected with a retrovial vector carrying the human γ-interferon gene. Each patient received six injections and the sera of both patients showed a humoral response against the autologous tumor cells as measured by a fluorescence-activated cell sorter (FACS) and solid phase radioimmunoassay (RIA).

After the last injection, 120 ml of blood was removed and the PBL were isolated by centrifugation in Ficoll Hypague.

The PBL from DM414 were used without fractionation to construct the 414 scFv library. The PBL from DM341 were fractionated by absorption to a culture of autologous melanoma cells growing in a 75 cm$^2$ flask; after 30 min the unabsorbed PBL were collected and used to construct the DM341-II scFv library. The melanoma cells were then rinsed twice with culture medium, and the PBL that remained bound to the cells were used to construct the DM341-I scFv library.

The PBL fraction that bound to the melanoma cells should be enriched for B cells producing membrane-bround IgM, and anti-melanoma antibodies and the other containing the rest of the PBL population should include the mature B cells producing secreted IgG antibodies. As described in detail below, the heavy-chain segments of the scFv cDNAs were synthesized from both the IgM and IgG classes of mRNA for the DM341-I and DM414 libraries, and entirely from the IgG class for the DM341-II library. Thus the scFv antibodies encoded by each library should correspond mainly to anti-melanoma IgM for DM341-I, entirely to IgG for DM341-II, and to IgM and IgG for DM414.

Construction of scFv libraries. The protocol involves four consecutive steps, as follows: 1) Synthesis of the entire repertoire of first-strand cDNAs from the poly (A)+RNA of the melanoma patient's PBL. 2) Synthesis by polymerase chain reaction (PCR) of the $V_H$-$C_{H1}$ heavy chain genes for IgG and IgM classes, and the κ and λ light chains genes, adding complementary coding sequences for a peptide linker at the 3'-end of the heavy chain genes and the 5'-end of the light chain genes. 3) Synthesis by PCR of the $V_H$-linker-variable region light chain ($V_L$) scFv cDNAs. 4) Ligation of the scFv cDNAs into the filamentous phage vector fUSE5, which encodes the complete genome of the phage. Each resulting fusion-phage virion should display 4 or 5 copies of a scFv molecule conjugated to the envelop protein p3.

Poly (A)+RNA was isolated from the two PBL samples, and first-strand cDNAs were synthesized with random hexamers and oligo dT primers, using kits purchased from Invitrogen and BRL. The coding regions for the $V_H$- $C_{H1}$ heavy chains, and for the κ and λ light chains, were separately amplified by PCR using the following primers, which are based, in part, on procedures published by Marks, et al., cited above:

A. Constant region forward-primers

IgG: GTCCACCTTG GTGTTGCTGG GCTT (SEQ ID NO 1)

IgM: TGGAAGAGGC ACGTTCTTTT CTTT (SEQ ID NO 2)

$C_κ$: AGACTCTCCC CTGTTGAAGC TCTT (SEQ ID NO 3)

$C_λ$: TGAAGATTCT GTAGGGGCCA CTGTCTT (SEQ ID NO 4)

B. $V_H$ back-primers with SfiI site $V_H$ 1,4,6: ATGGCTCAGG GTTCGGCCGA CGTGGCCCAG GTRCAGCTGS WGSAGTCKGG (SEQ ID NO 5)

$V_H$ 2: ATGGCTCAGG GTTCGGCCGA CGTGGCCCAG GTCAACTTAA GGGAGTCTGG (SEQ ID NO 6)

$V_H$ 3,5: ATGGCTCAGG GTTCGGCCGA CGTGGCCGAG GTGCAGCTGK TGSAGTCTGS (SEQ ID NO 7)

C. $V_κ$ back-primers with linker $V_κ$ 1,4: GGCTCGGGCG GTGGTGGGTC GGGTGGCGGC GGATCTGACA TCSWGATGAC CCAGTCTCC (SEQ ID NO 8)

$V_κ$ 1,3,6: GGCTCGGGCG GTGGTGGGTC GGGTGGCGGC GGATCAGAWR TTGTGMTGAC KCAGTCTCC (SEQ ID NO 9)

$V_κ$ 5: GGCTCGGGCG GTGGTGGGTC GGGTGGCGGC GGATCAGAAA CGACACTCAC GCAGTCTCC (SEQ ID NO 10)

D. $V_λ$ back-primers with linker $V_λ$ 1,2: GGCTCGGGCG GTGGTGGGTC GGGTGGCGGC GGATCACAGT CTGYSYTGAC KCAGCCGCC (SEQ ID NO 11)

$V_λ$ 3a,3b: GGCTCGGGCG GTGGTGGGTC GGGTGGCGGC GGATCATCYT MTGWGCTGAC TCAGSMACC (SEQ ID NO 12)

$V_λ$ 4,5: GGCTCGGGCG GTGGTGGGTC GGGTGGCGGC GGATCACASG YTRTACTGAC TCAACCGYC (SEQ ID NO 13)

E. $J_H$ forward-primer with linker GCCACCCGAC CCACCACCGC CCGAGCCACC GCCACCTGAR GAGACGGTGA CCRKKGTYCC (SEQ ID NO 14)

F. $J_L$ forward-primers with SfiI site $J_κ$ 1: AGTCTAACGT TCGGCCCCAG CGGCCCCACG TTTGATYTCC ASCTTGGTCC C (SEQ ID NO 15)

$J_κ$ 2: AGTCTAACGT TCGGCCCCAG CGGCCCCACG TTTKATMTCC ASYYKKGTCC C (SEQ ID NO 16)

$V_λ$: AGTCTAACGT TCGGCCCCAG CGGCCCCACC TARRACGGTS ASCTKGGTCC C (SEQ ID NO 17)

The sequences are written 5' to 3'. Forward primers are complementary to the sense strand, and back primers are complementary to the antisense strand. Degenerate nucleotides are indicated as follows: Y=C or T; R=A or T; W=or T; S=or G; K=T or G; M=or C.

Each PCR mixture contained 2 µl from the first-strand cDNA syntheses, 50 pM of a constant region forward-primer, 50 pM of a back-primer, 250 µM dNTPs and 2.5 units Taq polymerase in buffer as provided (Boehringer Mannheim). A "touchdown" PCR protocol (Don, R. H., et al., (1991) *Nucleic Acids Res.* 19, 4008–4012) was used, as follows: 3 cycles each of denaturation at 94° C. for 1 min, annealing for 2 min, and elongation at 74° C. for 3 min; the annealing temperature was varied from 55° C. to 46° C. in steps of 1° C. The "touchdown" cycles were followed with 10 cycles of annealing at a temperature of 45° C. and a 10-min extension at 74° C. The PCR products were purified by electrophoresis in 1 agarose gel and extraction from the gel using the Qiaex kit (Qiagen); the purified DNAs were dissolved in 40 µl Tris/EDTA (TE; 10 mM Tris, pH 8.0/1 mM EDTA) buffer.

For the next PCR step, the joining-region heavy chain ($J_H$) forward-primers listed above were used in combinations with the $V_H$ back-primers, and the $J_L$ forward primers were used in combinations with the $V_κ$ and $V_λ$ primers. The PCR reagents and conditions were the same as above, except that the primer concentrations were 10 pM and the reaction involved 30 cycles at 94° C. for 1 min, 54° C. for 1 min and 72° C. for 1 min followed by extension at 72° C. from 10 min. The PCR products were purified as above.

The complete scFv molecules were synthesized by PCR as follows: 10 ng each of the $V_H$ and $V_L$ cDNAs were added to 100 µl of PCR reagents and cycled 7 times at 94° C. for 1 min, 60° C. for 1 min and 72° C. for 2 min. to form $V_H$-linker-$V_L$ molecules. Then 10 pM of the $V_H$ back primers and 10 pM of the $J_L$ forward primers were added and cycled again 25 times. The products were precipitated with ethanol and purified by electrophoresis in 1% LMT agarose gel and extraction with β-agarase (New England Biolabs).

The scFv cDNAs and the RF DNA of the fUSE5 vector were digested with SfiI and purified by electrophoresis in 1% LMT agarose gel. Ligation of the cDNA with the vector DNA was done in 100 μl reaction mixture containing 1.5 μg cDNA, 8 μg vector DNA and 2000 units T4 DNA ligase for 16 hours at 16° C.

The ligation products were purified by extraction with phenol/chloroform and precipitation with ethanol, and were dissolved in 20 μl of water. The entire purified DNA sample was used to transform DH10B ElectroMax cells (GIBCO BRL), and the cells were plated on 2× TY agar medium supplemented with 12.5 μg/ml tetracycline in 24×42 cm trays. The total number of transformed cell colonies was about $4 \times 10^7$ for the DM341-I library, $5 \times 10^8$ for the DM341-II library and $2 \times 10^8$ for the DM414 library. The colonies were collected in 2× TY medium supplemented with 12.5 μg/ml tetracycline, cultured for 1 hour at 37° C., and the cells were pelleted. The medium was passed through a 0.45 mm filter, and the filtrate, which constituted the scFv library, was stored at 4° C.

Composition of the scFv libraries. Both IgM and IgG $V_H$ genes were synthesized for the DM341-I and DM414 libraries, and only IgG $V_H$ genes were synthesized for the DM341-II library. The 341-I library is expected to contain mainly IgM $V_H$ genes, since the PBL fraction that bound to DM341 cells was used for the construction of the library. All of the libraries contained λ and κ $V_L$ genes. The fraction of phage with scFv inserts was determined by PCR synthesis, using primers complementary to phage sequences flanking the insert. The PCR products corresponded to a full-length scFv insert in about 85% of the randomly selected phage clones from each library; in about 10% of the clones the PCR product was truncated.

Human cells. a) Endothelial cells were isolated from umbilical cords and cultured; the cells were used after 2 to 6 transfers. b) Melanocytes were isolated from foreskins and cultured; the cells were used after 1 to 4 transfers. c) Melanoma lines DM341 and DM414 correspond to the autologous tumor cell lines used in the immunization of the patients described above. Other melanoma lines employed were cultures denoted DM 343, ZAZ and SIT1. SIT1-TF2 was a sub-culture of SIT1 which was transduced with the human tissue factor gene. d) Pancreatic carcinoma lines HPAF, Capan-2 and Colo357 were employed. e) The breast carcinoma lines are denoted SK-BR-3 and BT-20. f) The glioma line was Hs683. g) The ovarian carcinoma lines were SK-OV-3 and Hey. h) The colorectal carcinoma lines were HT-29 and Ls180. i) The prostate carcinoma line was DU145. j). The gastric carcinoma line was MS. k) The renal carcinoma line was Caki-1. Most of the carcinoma lines are available from the A.T.C.C. Culture medium for the melanoma and carcinoma lines was Dulbecco's modified Eagle's medium (DMEM)/10% fetal calf serum (FCS)/penicillin and streptomycin.

Panning a scFv library. The autologous melanoma lines were grown as an attached monolayer in 24-cm² flasks until almost confluent, and after changing the culture medium 3 times, the cells were incubated for 1 hour at 37° C. For the first panning step, the phage from a scFv library were precipitated in 4% PEG/0.5 M NaCl and resuspended in water, and about $10^{11}$ TU were added to the autologous melanoma cells in 2 ml DMEM/10% FCS. The culture flask was shaken gently for 2 hours at room temperature and then the medium was removed and the cells washed rapidly 10 times with phosphate buffered saline (PBS) at room temperature. The phage that remained attached were eluted to the cells in 2.0 ml E-buffer (0.1M glycine pH 2.2/0.1% BSA) for 10 min at room temperature and neutralized with 0.375 ml N-buffer (1M Tris-HCl, pH 9.1). The eluted phage were mixed with 15 ml of logphase *Escherichia coli* K91 Kan cells, and after 30 min at room temperature, the cells were plated on 2× TY agar/tetracycline at 12.5 μg/ml to amplify the phage. For each subsequent panning step the amplified phage from the previous panning step were precipitated in 4% PEG/0.5M NaCl and resuspended in water, and about $10^{11}$ phage were used to pan against autologous melanoma cells as described for the first panning step. After overnight incubation at 37° C, the colonies were collected in 2× TY/tetracycline at 12.5 μg/ml medium and cultured for 1 hr at 37° C. The cells were pelleted and the medium was passed through a 0.45-mm filter.

Cloning the phage. After each panning step, the eluted phage before amplification were mixed with *E. coli* K91 Kan cells at low phage-to-cell ratios, and the cells were plated on 2X TY/tetracycline agar and incubated overnight. Individual colonies were inoculated into 2× TY/tetracycline medium and grown overnight with shaking; the cells were pelleted and the medium containing the cloned phage stock was stored at 4° C. for ELISA assays.

Absorption against melanocytes. Melanocytes were grown in 35-mm culture dishes until a confluent layer had formed, and the cells were then fixed with gluteraldelhyde as described for ELISA reaction and blocked with DMEM/FCS. After panning, about 10% of the unamplified phage were added to the melanocytes in DMEM/10% FCS and kept at room temperature for 1 hr with gentle shaking. The unabsorbed phage were then transferred to a fresh culture dish containing fixed melanocytes and the procedure was repeated. After 10 such absorption steps, the unabsorbed were cloned.

ELISA assays. The cells were grown in 96-well plates (Falcon #3072) until almost confluent, washed with PBS and fixed with 0.24% glutaraldehyde for 30 min at room temperature. The fixed cells were washed with PBS and the wells were filled with DMEM/10% FCS and kept for 1 hour at room temperature. The wells were emptied and 200 μl of a stock of cloned phage supplemented with 1% BSA was added to each well and kept for 2 hours at room temperature. The wells were washed rapidly 10 times with PBS, and the amount of bound phage was assayed using a peroxidase-conjugated anti-M13 polyclonal antibody and o-phenylenediamine as the peroxidase substrate (Pharmacia Detection Module) following the protocol provided. Absorbance was read at 490 nm. All assays were done in triplicate.

Restriction analysis of scFv cDNAs. The cDNA insert in a phage clone was synthesized by PCR, using the 5'-primer ATTATTATTCGCAATTCCTTTAG (SEQ ID NO 18) and the 3'-primer GAATTTTCTGTATGAGGTTTTGCT (SEQ ID NO 19); these primers hybridize to phage sequences flanking the insert. The purified scFv product was digested separately with AluI for the clones from the DM341 libraries, and with Sau3AI and HinfI for the clones from the DM414 library. The digests were analyzed by electrophoresis in 1.5% agarose gel.

Binding studies. Each library was panned against live cultures of the autologous melanoma cells, and after each panning step individual phage randomly selected were cloned and tested by ELISA for binding to the autologous melanoma cells to obtain the following results:

|         | Clone |    |     |         |    |     |       |    |     |
| Panning | DM341-I |  |     | DM341-II |  |     | DM414 |    |     |
| step    | −  | +  | ++  | −  | +  | ++  | −  | +  | ++  |
| 0 | 20 | 0  | 0   | 20 | 0  | 0   | 20 | 0  | 0   |
| 1 | 41 | 7  | 0   | 43 | 6  | 0   | 46 | 0  | 1   |
| 2 | 41 | 1  | 6   | 24 | 9  | 14  | 54 | 25 | 719 |
| 3 | 20 | 16 | 487 | 45 | 16 | 517 |    |    |     |

Panning step 0 represents data from the original library. ELISA readings were scored as—for OD<0.05, + for OD 0.05–0.5, and ++ for OD>0.5.

The data indicate a significant enrichment at each panning step for such clones, with more than 90% showing a strong ELISA reaction after the third step for the DM341 libraries and after the second step for the DM414 library. Some of the phage from the last panning step were absorbed against cultured melanocytes to remove phage that react with melanocytes.

The phage clones that showed a strong ELISA reaction with the autologous melanoma cells were further tested by ELISA with cultured human endothelial and fibroblast cells, in order to identify clones that do not react, or react weakly, with two normal cell types, as an indication that the encoded antibodies are at least partly specific for the melanoma cells. The frequency of these clones was 21/517 from the DM341-II library, 18/719 from the DM414 library and 0/487 from the DM341-I library. Thus all of the more specific anti-melanoma antibodies were isolated from the two libraries which contain IgG $V_H$ genes, and none from the library which contains mainly IgM $V_H$ genes.

Since some of these antibodies could be identical, having been selected from scFv libraries containing multiple copies of phage with the same scFv cDNA insert, the insert in each clone was first analyzed by restriction mapping to identify inserts with different restriction patterns which should encode different antibodies. One representative clone for each of the different antibodies, seven from the DM341-II library and six from the DM414 library, was chosen for further ELISA tests against a panel of human tumor lines. The panel contained melanoma, glioma, pancreatic, breast, ovarian, colon, prostate and gastric tumor lines, and also cultured normal melanocyte, endothelial and fibroblast cells (Table 1).

TABLE 1

ELISA assays of selected anti-melanoma scFv fusion-phage clones for binding to cultured tumor lines and normal cells.

| ELISA assay, relative binding unit | | | | | | | | | | | |
|---|---|---|---|---|---|---|---|---|---|---|---|
| | Melanoma | | | | | | | | | Ovarian | |
| Clone | 1 | 2 | 3 | 4 | 5 | Endothelial | Fibroblast | Melanocyte | Glioma | 1 | 2 |
| 84   | 1.81 | 1.71 | 1.79 | 1.74 | 1.88 | 1.35 | 1.85 | 1.71 | 1.81 | 1.61 | 1.89 |
| D5   | 1.16 | 0.42 | 0.50 | 0.68 |      | 0.06 | 0.01 | 0.21 | 0.35 | 0.00 | 0.00 |
| D33  | 1.15 | 0.54 | 0.47 | 0.67 |      | 0.06 | 0.02 | 0.32 | 0.58 | 0.04 | 0.03 |
| Z78  | 0.75 | 0.16 | 0.26 | 0.43 |      | 0.05 | 0.05 | 0.20 | 0.36 | 0.01 | 0.01 |
| G57  | 1.20 | 0.52 | 0.58 | 0.79 |      | 0.08 | 0.01 | 0.36 | 0.40 | 0.01 | 0.00 |
| H18  | 1.17 | 0.36 | 0.45 | 0.66 |      | 0.05 | 0.02 | 0.26 | 0.45 | 0.02 | 0.00 |
| K2   | 0.58 | 0.20 | 0.30 | 0.43 |      | 0.00 | 0.01 | 0.20 | 0.21 | 0.02 | 0.01 |
| K10  | 0.56 | 0.24 | 0.52 | 0.18 |      | 0.03 | 0.05 | 0.14 | 0.65 | 0.11 | 0.16 |
| V13  | 1.04 | 1.51 | 0.73 | 1.19 | 1.11 | 0.00 | 0.04 | 0.04 | 0.90 | 0.02 | 1.61 |
| V73  | 0.04 | 0.14 | 0.02 | 0.69 | 0.30 | 0.00 | 0.01 | 0.03 | 0.84 | 0.02 | 1.58 |
| V86  | 0.87 | 0.92 | 0.38 | 0.74 | 0.59 | 0.00 | 0.02 | 0.03 | 0.01 | 0.00 | 0.00 |
| V373 | 0.58 | 0.65 | 0.98 | 0.87 | 0.80 | 0.07 | 0.05 | 0.46 | 0.53 | 0.50 | 0.14 |
| V474 | 0.40 | 1.76 | 1.04 | 1.60 | 1.71 | 0.00 | 0.05 | 0.00 | 0.32 | 0.01 | 0.73 |
| V575 | 0.77 | 0.88 | 0.87 | 0.26 | 0.59 | 0.06 | 0.00 | 0.15 | 1.57 | 0.07 | 0.57 |

| ELISA assay, relative binding unit | | | | | | | | | |
|---|---|---|---|---|---|---|---|---|---|
| | Breast | | Pancreatic | | | Colorectal | | | | |
| Clone | 1 | 2 | 1 | 2 | 3 | 1 | 2 | Gastric | Renal | Prostate |
| 84   | 1.81 | 1.66 | 1.62 | 1.91 | 1.79 | 1.83 | 1.83 | 1.80 | 1.73 | 1.71 |
| D5   | 0.07 | 0.00 | 0.00 | 0.00 | 0.00 | 0.01 | 0.00 | 0.00 | 0.00 | 0.00 |
| D33  | 0.08 | 0.01 | 0.00 | 0.06 | 0.07 | 0.06 | 0.13 | 0.09 | 0.07 | 0.03 |
| Z78  | 0.04 | 0.00 | 0.00 | 0.01 | 0.00 | 0.02 | 0.02 | 0.01 | 0.00 | 0.00 |
| G57  | 0.05 | 0.00 | 0.00 | 0.00 | 0.00 | 0.01 | 0.01 | 0.00 | 0.00 | 0.00 |
| H18  | 0.07 | 0.00 | 0.00 | 0.01 | 0.00 | 0.02 | 0.00 | 0.00 | 0.00 | 0.00 |
| K2   | 0.05 | 0.00 | 0.00 | 0.01 | 0.01 | 0.03 | 0.04 | 0.01 | 0.02 | 0.00 |
| K10  | 0.27 | 0.12 | 0.15 | 0.17 | 0.21 | 0.22 | 0.26 | 0.18 | 0.21 | 0.20 |
| V13  | 0.03 | 0.31 | 0.46 | 0.86 | 0.20 | 0.00 | 0.07 | 0.02 | 1.39 | 0.36 |
| V73  | 0.07 | 0.09 | 0.05 | 0.04 | 1.16 | 0.00 | 0.00 | 0.59 | 0.12 | 0.35 |
| V86  | 0.01 | 0.00 | 0.01 | 0.21 | 0.01 | 0.00 | 0.00 | 0.00 | 0.03 | 0.01 |
| V373 | 0.50 | 0.41 | 1.02 | 0.25 | 0.57 | 0.95 | 0.76 | 1.67 | 1.06 | 13.3 |
| V474 | 0.00 | 0.20 | 0.24 | 0.32 | 0.11 | 0.04 | 0.03 | 0.03 | 1.10 | 0.18 |
| V575 | 0.00 | 0.01 | 0.00 | 0.31 | 0.00 | 0.06 | 0.00 | 0.08 | 0.83 | 0.11 |

For each clone an equal aliquot from the same stock was used in all assays. Although stocks for all clones were prepared with the same procedure, phage titers could differ. Therefore, ELISA assays for each clone can be compared to obtain an estimate of the relative binding specificities of the clone for different cells. However, comparison of ELISA assays among different clones might not be significant. Clone 84 is a non-specific anti-melanoma control isolated from the panned DM341-II library. Clones D, G, H, K, and Z were isolated from the DM341-II library after the third panning step; D and Z clones were isolated before, and the others after, absorption to melanocytes. V clones were isolated from the DM414 library after the second panning step and absorption to melanocytes. ELISA values are the averages of three assays that generally agreed within 10%. Numbered cell lines are as follows: (i) melanoma—1, DM341; 2, DM343; 3, SIT1-TF2; 4, ZAZ; 5, DM414, (ii) ovarian—1, SK-OV-3; 2, Hey, (iii) breast—1, SK-BR-3; 2, BT-20, (iv) pancreatic—1, Hpaf; 2, Colo 347; 3, Capan-2, (v) Colorectal—1, HT-29; 2, Ls180. Other lines are identified above. Each ELISA plate included two wells used as a baseline, one containing cells only and another containing cells and a scFv clone, isolated from the original library, which did not show significant binding to any of the cell lines. The average of the ELISA readings of the two wells, which was generally <0.1, was subtracted from the readings of the other wells in the plate. All assays were done in triplicate, and agreement was generally within 10%.

Six of the clones from the DM341-II library (D5, D33, Z78, G57, H18, and K2) reacted strongly only with melanoma, melanocyte and glioma cells. Since these three cell types share a common developmental lineage from embryonic neural crest tissue, the six reactive antibodies appear to be specific for that lineage. The remaining clone K10 reacted also with the other tumor lines which have different lineages.

Four of the clones from the DM414 library (V13, V73, V86 and V474), in contrast to the clones from the DM341-II library, did not react, or reacted weakly, with melanocytes. Clone V86 shows the tightest association with melanoma, reacting strongly only with the melanoma lines and one pancreatic tumor line. Clones V13, V73 and V474 reacted with melanoma lines and also with several other tumor lines. The remaining clones V373 and V575 reacted with melanocytes as well as melanomas and other tumor lines, similar to clone K10 from the DM341-II library.

The clone binding with the panel of 21 human tumor lines, comprising melanomas and 8 other types of tumors, and also normal melanocyte, endothelial and fibroblast cells thus identifies three classes of anti-melanoma antibodies: One is a melanoma-specific class which shows a strong ELISA reaction almost exclusively with melanoma lines; the second is a tumor-specific class which shows a strong ELISA reaction with melanoma lines and several of the other tumor lines but not with normal melanocyte, endothelial or fibroblast cells; the third is a lineage-specific class which shows a strong ELISA reaction with the melanoma lines and melanocytes, and also with a glioma line which shares a common melanocytic lineage, but not with other tumor lines or with normal endothelial and fibroblast cells. Most of the antibodies reacted with all of the melanoma lines tested, and therefore appear to recognize antigens common to all human melanomas. The ELISA results for clone V86 were confirmed by immunohistochemistry, reacting biotin-labelled fusion phage with cell lines and staining with the ABC/DAB kit from Vector Laboratories.

Clone sequencing. Ten of the clones listed in Table 1 were sequenced. The complete sequence of the single-chain Fv cDNA insert in the fusion phage was determined for each clone. The sequences are set out in the Sequence Listings section as SEQ ID NOs 20 to 38. The sequences for the Complementary Determining Regions (CDR) for each clone are shown in Table 2 below. Note that V86 and V575 do not contain a complete light chain. Table 2. Amino acid sequences of the Complementary Determining Regions CDR1, CDR2 and CDR3 of selected cloned antibodies. These sequences are taken from the complete single-chain Fv sequences for each clone.

A. Heavy Chains

| Clone # | CDR1 | CDR2 | CDR3 |
|---|---|---|---|
| H18 | NHWFH | WVSPNTGATKYAEMFQG | AAGSSYYFGMDI |
| G57 | DYWMS | AISGSGGSTYYTDSVKG | EMNYFSHAMDV |
| D33 | NHWFH | WVSPNTGATKYAEMFQG | AAGSSYYFGMDI |
| Z78 | GHAMH | AISGNGGSTYYSDSVKG | DWYPDSWSGYAVDGLDV |
| V13 | SYAMS | AISGSGGSTYYADSVKG | GVAPFDY |
| V73 | SYWIG | IIYPGDSDTRYRPSFQG | LTPDDYGGNTPDY |
| V86 | SYAMS | AISGSGGSTYYADSVKG | GWGLRGEEGDYYMDV |
| .V373 | SSYIH | VINPSGGNTIYARNFQG | DRRYCSGGSCYAEVVY |
| .V474 | SYTMS | AISGSGGSTYYADSVKG | GVAPFDY |
| V575 | SYAMH | VISYDGSNKYYADSVKG | GFPYGGNSDYGMDV |

B. Light Chains

| Clone # | CDR1 | CDR2 | CDR3 |
|---|---|---|---|
| H18 | SGSSSNIGSNYVY | RNNQRPS | QSYDNSLNGYV |
| G57 | SGSSSNIGSNYVY | RNNQRPS | ASQDDSLRGYV |
| D33 | RSSQTLVFSDGHNYVN | ELSNRDP | IH/QGTLCPFT |
| Z78 | SGSSSNIGNNAVN | YDDLLPS | AAWDDSLNGP |
| V13 | RASQSISSYLN | KASSLES | QQYNSYSRT |
| V73 | SGSSSNIGNNVS | ENNKRPS | GTWDSSLSAEV |
| V86 | not present | not present | not present |
| V373 | SGSSSNIGNNYVS | ENNKRPS | QSYDSSLSGYV |
| V474 | RASQSISSYLN | KASSLES | QQYNSSSRT |
| V575 | not present | not present | not present |

The table uses the following abbreviations for the amino acid residues: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val, W, Trp; and Y, Tyr. Full amino acid sequences using the U.S. Patent Office format are set forth hereinafter in the Sequence Listing section of this application. Numbering corresponds as follows: In part A above, the CDR1, CDR2, and CDR3 fragments of the antibody heavy chains are respectively denoted residues 31 to 35, 50 to 66, and 99 to 110 of SEQ ID NO 20 for clone H18; residues 31 to 35, 50 to 66, and 98 to 108 of SEQ ID NO 22 for clone G57; residues 30 to 34, 49 to 65, and 98 to 109 of SEQ ID NO 24 for clone D33; residues 31 to 35, 50 to 66, and 89 to 105 of SEQ ID NO 26 for clone Z78; residues 31 to 35, 50 to 66, and 112 to 121 of SEQ ID NO 28 for clone V13; residues 31 to 35, 50 to 66, and 99 to 111 of SEQ ID NO 30 for clone V73H; residues 31 to 35, 50 to 66, and 99 to 118 of SEQ ID NO 32 for clone V86; residues 29 to 33, 47 to 63, and 96 to 111 of SEQ ID NO 34 for clone V373H; residues 31 to 35, 50 to 66, and 99 to 105 of SEQ ID NO 36 for clone V474; and residues 31 to 35, 50 to 66, and 99 to 112 of SEQ ID NO 38 for clone V575.

For part B above, the CDR1, CDR2, and CDR3 fragments of the antibody light chains are respectively denoted residues 23 to 35, 51 to 57, and 90 to 100 of SEQ ID NO 21 for clone H18L; residues 23 to 35, 51 to 57, and 90 to 100 of SEQ ID NO 23 for clone G57; residues 24 to 39, 55 to 61, and 94 to 102 of SEQ ID NO 25 for clone D33; residues 23 to 35, 51 to 57, and 88 to 97 of SEQ ID NO 27 for clone Z78; residues 24 to 34, 50 to 56, and 89 to 97 of SEQ ID NO 29 for V13; residues 24 to 36, 52 to 58, and 91 to 101 of SEQ ID NO 31 for V73; residues 23 to 35, 51 to 57, and 90 to 100 of SEQ ID NO 35 for V373; and residues 24 to 34, 50 to 60, and 93 to 101 for V474.

Note that since the lineage-specific class of anti-melanoma antibodies is an anti-self class, some or all of those antibodies might also be part of the normal anti-self repertoire of unimmunized persons. However, unlike the normal human anti-self repertoire which is composed mainly of IgM antibodies, the lineage-specific anti-melanoma antibodies are isolated from the 341-II library which contains only IgG $V_H$ genes, but not from the 341-I library which contains mainly IgM $V_H$ genes. IgG antibodies are generated in response to an antigenic stimulus, which for the melanoma patients in this study was the immunization with autologous tumor cells. Since there was a humoral response to the autologous tumor exhibited by the patients, the lineage-specific anti-melanoma antibodies appear to have been induced by the immunization. This conclusion is supported by the sequence analyses of the scFv genes for four of the lineage-specific antibodies, which show numerous differences in the CDR regions from the nearest germline V-genes.

The sequences show that, although the two immunized melanoma patients were treated with the same immunization protocol, different classes of anti-tumor antobodies are produced. Thus, the lineage-specific class was isolated from the 341-II library and the melanoma-specific class from the 414 library.

The sequences also show the variety of antibodies generated by the procedure, and indicate the enormous size of the untapped pool of antibodies that can be accessed from blood samples to expand the repertoire of human anti-tumor antibodies.

Example 2

A melanoma-specific $V_H$ antibody cloned from a fusion phage library of a vaccinated melanoma patient described in Example 1 was further investigated. Some of the research is set out in Cai, X., and Garen, A., *Proc. Natl. Acad. Sci.* 93:6280–6285 (1996).

As the previously described ELISA tests for binding of the V86 fusion phage to a panel of human metastatic melanoma and carcinoma cell lines and primary cultures of normal melanocytes, endothelial and fibroblast cells in Example 1 showed, measurable binding occurred only to the melanoma cells. The strict specificity of V86 for melanoma cells was confirmed by immunohistochemical staining tests with cultured cells and frozen tissue sections in this Example: The V86 fusion phage stained melanoma cell lines, but did not stain carcinoma cell lines or cultured normal cells; V86 also stained specifically the melanoma cells in sections of metastatic tissue but did not stain any of the cells in sections from normal skin, lung and kidney or from metastatic colon and ovarian carcinomas and a benign nevus.

An unexpected finding was that V86 contained a complete $V_H$ domain but only a short segment of a $V_L$ domain which terminated before the CDR1 region. This $V_L$ deletion resulted from the occurrence in the $V_L$ cDNA of a restriction site which was cleaved during construction of the scFv library. Thus V86 is essentially a $V_H$ antibody. The effect of adding a $V_L$ domain to V86 was examined by constructing scFv fusion phage libraries in which V86 was coupled to Vλ or Vκ domains from the original scFv library of the melanoma patient, and then panning the libraries against melanoma cells to enrich for the highest-affinity antibody clones. None of the V86 - Vλ clones showed significant binding to melanoma cells in ELISA tests; although binding occurred with most of the V86 -$V_K$ clones it was generally weaker than the binding of V86. These results indicate that most of the $V_L$ domains in the original scFv library reduce or eliminate the affinity of V86 for melanoma cells. V86 was further characterized by immunohistochemistry with cultured cells and tissue sections.

Human cells. Cell lines and isolates were as described in Example 1 above, except that melanoma line A2058 obtained from the A.T.C.C. was also employed.

Immunoperoxidase staining of cells and tissue sections. The cultured cells were grown in 16-well culture chambers (Lab-Tek Chamber Slide) until about 50% confluent, washed with PBS and fixed with 0.24% glutaraldehyde for 30 min at room temperature. The fixed cells were washed with PBS and the wells were filled with 2% FCS in PBS and kept for 1 hr at room temperature. The wells were emptied and 200 μl of a stock of cloned V86 fusion phage or fUSE5 control phage diluted 1:1 with 2% FCS in PBS was added to each well and kept for 2 hr at room temperature, and the wells were washed 3 times with PBS for 5 min each. The bound phage were detected by reacting first with a peroxidase-conjugated anti-M13 polyclonal antibody (Pharmacia) diluted 1:200 and then staining with a diaminobenzidine+H2O2 substrate (Vector Labs). Tissue sections cut from frozen samples of melanoma tumors or normal skin were attached to glass slides and fixed in 0.24% glutaraldehyde at room temperature for 10 min. The fixed sections were used for immunohistochemistry as described for cultured cells.

DNA sequencing. A single bacterium colony carrying a phage clone was inoculated into 50 ml 2×TY tet broth and grown overnight; the bacteria were removed by centrifugation and the supernatant medium was filtered through a 0.45 μm membrane. The phage in the medium were precipitated by adding 1/10 volume of a 20% polyethylene glycol 8000+ 2.5 M NaCl stock solution, and the phage were pelleted and resuspended in PBS. The precipitation procedure was repeated once and the phage pellet was resuspended in 100 μl water. The phage DNA was extracted twice with phenol+ chloroform and once with chloroform, and the DNA was precipitated with ethanol+NaAc and resuspended in 50 μl water. The primer for sequencing the $V_L$ domain was TGATTTTCTGTATGAGG (SEQ ID NO. 39) which hybridizes 90 bases away from the 5'-end of gene-3 of the phage; the primer for sequencing the $V_H$ domain was ACCCGAC-CCACCACCGCCCGA (SEQ ID NO. 40) which hybridizes to the linker of the scFv molecule.

Construction of V86-Vλ and V86-Vκ libraries. The cDNA encoding the $V_H$ domain of V86 was synthesized by PCR from the V86 fusion phage clone as described in Example 1. The sequence of the 5'-primer was ATTATTAT-TCGCAATTCCTTTAG (SEQ ID NO. 18) which hybridizes to the gene-3 of the phage, and the sequence of the 3'-primer was GCCACCCGACCCACCACCGCCCGAGC-CACCTGARGAGACGGTGACCRKKGTYCC (SEQ ID NO. 14) which includes part of the $J_H$ and linker sequences. The cDNAs encoding the Vκ and Vλ domains were synthesized from PBL of melanoma patient DM414 as described above. To construct the V86-Vκ and V86-Vλ scFv cDNAs the complementary linker sequences were hybridized and the cDNAs were synthesized by PCR. The procedure involved adding 10 ng of V86 cDNA and 10 ng of Vκ or Vλ cDNAs to 100 µl of PCR reagents and cycling seven times at 94° C. for 1 min, 60° C. for 1 min, and 72° C. for 2 min; 10 pM of a mixture of $V_H$ back-primers and 10 pM of Jκ or Jλ forward primers were then added and the PCR synthesis was continued for 25 cycles. The PCR products were precipitated with ethanol and purified by electrophoresis in 1% LMT agarose gel and extraction with β-agarase. To construct the fusion phage libraries, the scFv cDNAs and the replicative form of the fUSE5 DNA were digested with SfiI and ligated in 100 µl of reaction mixture containing 1.5 µg of scFv cDNA, 8 µg of vector DNA and 2000 units of T4 DNA ligase for 16 hrs at 16° C. The ligation products were purified by extraction with phenol+chloroform and precipitation with ethanol, and the purified DNA was used to transform DH10B ElectroMax cells (GIBCO/BRL). The cells were plated on 2×TY tet agar. The total number of transformed clones was $4 \times 10^7$ for the V86-Vκ library and $1 \times 10^8$ for the V86-Vλ library. The fusion phage stocks for each library were prepared from the transformed cells. The fraction of phage with scFv inserts, as determined by PCR synthesis using primers complementary to phage sequences flanking the insert, was 75% (15/20) for the V86-Vκ library and 83% (19/23) for the V86-Vλ library.

Panning the V86-Vκ and V86-Vλ libraries. The melanoma cell line A2058 was grown as an attached monolayer in 24 cm² flasks until almost confluent, washed with PBS and fixed with 0.24% glutaraldehyde for 10 min at room temperature. The fixed cells were washed with PBS and blocked with DMEM+10% FCS for 1 hr at room temperature. The phage from the V86-Vκ and V86-Vλ libraries were precipitated in 4% PEG+0.5 M NaCl and resuspended in water, and about $10^{11}$ phage in 2 ml DMEM+10% FCS were added to the melanoma cells. The culture flask was shaken gently for 2 hr at room temperature and the medium was removed and the cells washed rapidly 10 times with PBS at room temperature. The attached phage were eluted from the cells in 2 ml of E-buffer for 10 min at room temperature and immediately neutralized with 0.375 ml N-buffer (2). The eluted phage were mixed with 15 ml of *E. coli* K91 Kan cells and after 30 min at room temperature the cells were plated on 2×TY tet agar. The colonies were collected in 50 ml 2×TY tet medium and incubated for 1 hr. The bacteria were pelleted and the supernatant medium was filtered through a 0.45 µm membrane. For each subsequent panning step the amplified phage from the previous panning step were precipitated in 4% PEG+0.5 M NaCl and resuspended in water, and about $10^{11}$ TU of the phage were used for panning against melanoma cells A2058 as described for the first panning step.

Preparation of fusion phage clones. The phage were mixed with *E. coli* K91 Kan cells at low phage to cell ratios and the cells were plated on 2×TY tet agar. Individual colonies were inoculated into 2 ml 2×TY tet medium and grown overnight. The cells were pelleted and the medium containing the cloned phage was used for the initial ELISA assays. The medium was filtered through a 0.45 µm membrane and precipitated in 4% PEG+0.5 M NaCl twice. The phage titer in each cloned stock was determined and adjusted to contain $10^{10}$ phage transforming units (TU) per ml.

ELISA assays. The cells were grown in 96-well microtiter plates until almost confluent, washed with PBS and fixed with 0.24% glutaraldehyde for 30 min at room temperature. The fixed cells were washed with PBS, and the wells were filled with DMEM+10% FCS and kept for 1 hr at room temperature. The wells were emptied and 100 µl of a stock of cloned phage diluted 1:1 with DMEM+10% FCS was added to each well. After 2 hr at room temperature the wells were washed rapidly 10 times with PBS and the amount of bound phage was assayed using a peroxidase-conjugated anti-M13 polyclonal antibody and O-phenylenediamine as the peroxidase substrate (Pharmacia Detection Module). All assays were done in triplicate.

Restriction analysis of V86-Vκ and V86-Vλ cDNAs. The cDNA insert in a phage clone was synthesized by PCR using the 5'-primer ATTATTATTCGCAATTCCTTTAG (SEQ ID NO. 18) and the 3'-primer GAATTTTCTGTATGAG-GTTTTGCT (SEQ ID NO. 19) which hybridize to phage sequences flanking the insert. The purified cDNA products were digested separately with Sau3AI and HinfI, and the digests were analyzed by electrophoresis in 2% agarose gel.

Results. The antibody V86 was selected from a scFv fusion phage library of a melanoma patient by panning against the autologous tumor cells. Previous ELISA tests with a panel of melanoma lines, carcinoma lines and primary cultures of normal cell types including melanocytes showed that V86 fusion phage could bind to the melanoma cells but not to the carcinoma cells or normal cells (Example 1). The melanoma-specific binding of V86 was further tested by immunohistochemistry with several of the tumor cell lines and normal cells used for the ELISA tests. V86 showed a staining reaction with the melanoma cells but not with either the carcinoma cells or normal cells, confirming the ELISA results. Because the reaction of V86 with melanoma cells might involve an antigen expressed by the cultured cells but not by melanoma tumors in vivo, additional immunohistochemistry was done with sections of frozen human metastatic melanoma tissue and normal skin tissue. V86 showed a staining reaction with the melanoma tissue but not with the connective tissue in the melanoma sections or with any of the tissues in the section of normal skin; V86 also failed to stain any of the tissues in sections of frozen normal lung and kidney or of metastatic colon and ovarian carcinomas and a benign nevus. These results demonstrate that V86 can bind specifically to melanoma cells in a metastatic tumor as well as to cultured melanoma cells. The staining of the melanoma sections appears to concentrate along the borders of the melanoma cells, suggesting that the antibody binds at the cell surface.

The sequence of the V86 antibody, as deduced from the sequence of the cDNA insert in the fusion phage, shows a complete $V_H$ domain followed by the linker which couples the $V_H$ and $V_L$ domains in a scFv molecule; however the $V_L$ domain terminates before the CDR1 region (Table 3).

TABLE 3

Amino Acid Sequence of Clone V86.

| FR1 | CDR1 | FR2 | CDR2 |
|---|---|---|---|
| QVQLVQSGGGLVQPGGSGRGSCAASGFTFS | SYANS | WVRQAPGKGLEWVA | AISGSGGSTYYADSVKG |

| FR3 | CDR3 | FR4 |
|---|---|---|

TABLE 3-continued

Amino Acid Sequence of Clone V86.

```
RFTISRDNSKNTLYLQMNSLRAEDTAVYYCAR GWGLRGEEGDYYMDV WGKGTMVTVSS

LINKER              FR1
GGGGSGGGGSGGGGS SYELTQEPRGGGTQLTVLGGAAGA
```

The complete $V_H$ domain is followed by the linker (SEQ ID NO 32) and the truncated $V_L$ domain (SEQ ID NO 33).

The reason for the premature termination of the $V_L$ domain is the presence of an SfiI restriction site which was cut in the process of cloning the V86 scFv cDNA into the fusion phage, resulting in the deletion of the distal $V_L$ segment.

The next series of experiments was designed to test the effect of adding a $V_L$ domain to V86 on the specificity and affinity of the antibody for melanoma cells. Two scFv fusion phage libraries were constructed for this purpose, one expressing V86-Vκ antibodies and the other V86-Vλ antibodies. The Vκ and Vλ domains for these libraries were derived from the repertoire of $V_L$ domains in the original scFv library used for the isolation of V86. Individual clones were isolated from each library, and those containing different Vλ or Vκ domains, as determined by restriction mapping the cDNAs in the fusion phage, were tested by ELISA for binding to the melanoma cell line A2058 (Table 4).

TABLE 4

Effect of Different Vλ and Vκ Domains on the Binding of V86 to Melanoma Cells.

| clones | ELISA absorbance | | | |
|---|---|---|---|---|
| | +++ | ++ | + | − |
| V86-Vλ | 0 | 0 | 0 | 50 |
| V86-Vκ | 2 | 20 | 28 | 18 |

The V86-Vλ and V86-Vκ clones are random isolates from the two fusion phage libraries, each expressing the V86 $V_H$ domain linked either to Vλ or Vκ domains from the original scFv library. The melanoma cell line for the ELISA tests was A2058. The ELISA absorbance scales are as follows: +++ > 0.8; ++ 0.8–0.5; + 0.5–0.1; − < 0.1. The absorbance for V86 without a $V_L$ domain is 1.0.

None of the V86-Vλ clones showed detectable binding, indicating that Vλ domains are incompatible partners for V86; most of the V86-Vκ clones showed significant binding but it was generally weaker than the binding of V86. Thus most of the $V_L$ partners for V86 reduce or eliminate its capacity to bind to melanoma cells. The V86-Vλ and V86-Vκ libraries were then panned twice against melanoma cells to enrich for any higher affinity antibodies which might be present, and clones of the panned phage containing different Vλ or Vκ domains were tested by ELISA for binding to the melanoma line A2058. As before, binding occurred with the V86-Vκ clones and not with the V86-Vλ clones. The relative binding affinities for melanoma cells of 15 panned V86-Vκ clones were compared with V86, using a Scatchard plot assay to determine Kd values for binding to a melanoma cell line. The relative binding affinity was highest for V86, indicating that V86 functions more effectively as a $V_H$ than as a scFv anti-melanoma antibody. The panned V86-Vκ clones were also tested by ELISA for specific binding to melanoma cells, using a panel of cells consisting of the melanoma line A2058, 4 carcinoma lines and primary cultures of melanocyte, endothelial and fibroblast cells. All of the V86-Vκ clones bound only to the melanoma cells, indicating that addition of a Vκ domain to V86 affects only its affinity but not its specificity for melanoma cells.

Discussion. The strict specificity of the human antibody V86 for melanoma cells first demonstrated by ELISA tests with a panel of human melanoma and carcinoma cell lines and primary cultures of normal cells including melanocytes reported in Example 1 was confirmed by immunohistochemistry with the tumor lines and cultured normal cells and also with frozen sections of metastatic melanoma and carcinoma tissues, a benign nevus and three normal tissues including skin: V86 reacted specifically with melanoma cells in the melanoma tissue and cell lines and did not react with any of the normal cells or other tumor cells or the benign nevus. V86 appears to bind to a cell surface antigen expressed by all of the metastatic melanomas tested and not by normal cells or other tumors.

Although V86 was isolated from a fusion phage library designed to display the antibody repertoire of a cancer patient as scFv molecules and therefore should have contained both a $V_H$ and $V_L$ domain, most of the $V_L$ domain is missing because an extraneous cloning site located near the 5'-end of the $V_L$ cDNA was cleaved during construction of the library, resulting in a deletion of the distal $V_L$ region. Despite the absence of a $V_L$ partner V86, appears to be one of the most specific anti-melanoma antibodies isolated from the library. It was shown in other studies that an isolated heavy chain of a monoclonal antibody can retain the specificity of the intact antibody for its cognate determinant, although the affinity is usually reduced by one or two orders of magnitude (Haber, E. & Richards, F. F., (1963) Proc. Royal Soc. Series B 166, 176–187 and Jaton, J. C., et al. (1968) Biochem. 7, 4185–4195). A similar finding was reported for $V_H$ antibodies synthesized from spleen DNA of mice immunized with lysozyme: The specificity for lysozyme was retained but the affinity was about 10-fold weaker as compared to a complete monoclonal anti-lysozyme antibody Ward, E. S., et al. (1989) Nature 341, 544–5467). To determine the effect of linking a $V_L$ domain to V86 on its specificity and affinity for melanoma cells, two scFv fusion phage libraries was constructed, expressing the V86 domain in random pairwise combinations with either Vλ or Vκ domains derived from the original scFv library used for the isolation of V86. All of the different Vλ domains tested as partners for V86 prevented binding to melanoma cells; binding occurred with most of the different Vκ domains tested but it was generally weaker than the binding of V86. Thus the V86 single-domain $V_H$ antibody binds more strongly to melanoma cells than do most of the V86 scFv antibodies containing randomly paired $V_L$ domains. Although the affinity of V86 for melanoma cells is usually reduced by addition of a Vκ domain, the strict specificity for melanoma cells is not affected, consistent with other evidence that the $V_H$ domain alone can determine antibody specificity.

The anti-tumor antibodies expressed by the mature B cells in the PBL of vaccinated cancer patients, such as the patient from whom V86 was derived, have probably been subjected to affinity maturation which optimizes the specificity and affinity of an antibody for its cognate determinant. However, because construction of a scFv or Fab library involves random pairings between highly complex populations of $V_H$ and $V_L$ cDNAs, there is virtually no chance that the original combination of $V_H$ and $V_L$ partners for any antibody will be included in a library of the usual size. Pairing a $V_H$ domain with a new $V_L$ partner usually results in a less active or inactive antibody, as shown here for V86. Consequently $V_H$ domains that could function as anti-tumor $V_H$ antibodies might remain undetected in single scFv or Fab libraries because of an incompatible $V_L$ partner. To test whether random combinatorial antibody libraries might be circumvented by using $V_H$ libraries to pan for anti-tumor antibodies, a $V_H$ fusion phage library containing the same population of $V_H$ genes as the scFv library used for the isolation of V86 was investigated as described in Example 3, which illustrates that additional melanoma-specific antibodies can be cloned from the $V_H$ library.

A natural repertoire of functional heavy chain antibodies has been reported in the camel (Hammers-Casterman, C., et al. (1993) *Nature* 363, 446–448). The antibodies are composed of two identical disulfide-linked heavy chains each containing a $V_H$, $C_H2$ and $C_H3$ domain. The camel also has a minor population of antibodies with the expected composition of two complete heavy chains and two complete light chains. This remarkable discovery raises intriguing questions concerning the evolutionary and functional significance of heavy chain antibodies. It also provides additional evidence that a functional antibody need not contain a $V_L$ domain.

Example 3

In most mammalian antibodies the variable domain of the heavy chain ($V_H$) and the light chain ($V_L$) interact to form the combining site for the cognate epitope. A notable exception is the antibody repertoire of the camel, which consists mostly of molecules containing two heavy chains but no light chains. The heavy chain camelid antibodies react with a broad spectrum of antigens in a trypanosome lysate, indicating that the immune system of the camel can generate a diverse repertoire of functional antibodies devoid of a light chain. Earlier studies with isolated heavy and light chains of several mouse monoclonal antibodies had shown that the binding specificity resided entirely in the heavy chain, the light chain contributing only to the affinity. With the introduction of PCR technology for synthesizing the variable domains of antibodies, the specificity and affinity of $V_H$ and $V_L$ domains either alone or coupled in an Fab or scFv molecule could be analyzed. Several such studies have demonstrated the dominant role of $V_H$ domains in determining antibody specificity, and in some cases the affinity of the $V_H$ domain alone was comparable to the affinity of the complete antibody.

The cloning of the melanoma-specific antibody V86 from a scFv fusion phage library of a melanoma patient vaccinated with autologous tumor cells that were transfected with interferon-gamma gene was described above. Although V86 was isolated from a scFv library it is essentially a $V_H$ antibody because an extraneous cloning site located near the 5'-end of the $V_L$ cDNA was cleaved during construction of the library, resulting in a deletion of the distal $V_L$ region. The ability of V86 to function as a scFv antibody was tested by randomly conjugating to V86 $V_L$ domains from the antibody repertoire of the same patient. All of the $V_L$ domains tested as partners for V86 either reduced or eliminated its affinity for melanoma cells, indicating that V86 functions better as a $V_H$ than as a scFv anti-melanoma antibody. This result suggests that $V_H$ libraries could provide access to tumor-specific antibodies that might not be detected in scFv or Fab combinational libraries because of the incompatibility of most randomly paired $V_H$ and $V_L$ domains. In this Example, a $V_H$ and a scFv fusion phage library constructed from the antibody repertoire of a vaccinated melanoma patient as a source of melanoma-specific antibodies are compared. The results of this comparison demonstrate that melanoma-specific antibodies containing $V_H$ domains with distant CDR regions can be cloned froom the two libraries.

A $V_H$ and a scFv fusion phage library was constructed from the antibody repertoire of the vaccinated melanoma patient DM414 described above. Poly (A)$^+$ RNA was isolated from the PBL samples, and first-strand cDNAs were synthesized with random hexamers and oligo dT primers, using kits purchased from Invitrogen and BRL. The coding regions for the $V_H$-$C_{H1}$ heavy chains were amplified by PCR using the primers below:

A. Constant region forward-primer of IgG: GTC CAC CTT GGT GTT GCT GGG CTT (SEQ ID NO. 41)

b. $V_H$ back-primers with SfiI site:

$V_H$ 1,4,6: ATG GCT CAG GGT TCG GCC GAC GTG GCC CAG GTR CAG CTG SWG SAG TCK GG (SEQ ID NO. 42)

$V_H$ 2: ATG GCT CAG GGT TCG GCC GAC GTG GCC CAG GTC AAC TTA AGG GAG TCT GG (SEQ ID NO. 43)

$V_H$ 3,5: ATG GCT CAG GGT TCG GCC GAC GTG GCC GAG GTG CAG CTG KTG SAG TCT GS (SEQ ID NO. 44)

Each PCR mixture containing 2 µl from the first-strand cDNA synthesis, 50 pM of a constant-region forward-primer, 50 pM of a bck-primer, 250 µM dNTPs, and 2.5 units of Taq polymerase in buffer as provided (Boehringer Mannheim).

A "touchdown" PCR protocol was used as follows: three cycles each of denaturation at 94° C. for 1 minute, annealing for 2 minutes, and elongation at 74° C. for 3 minutes; the annealing temperature was varied from 55° C. to 40° C. in steps of 1° C. The "touchdown" cycles were followed with 10 cycles of annealing to a temperature of 45° C. and a 10-minute extension at 74° C. The PCR products were purified by electrophoresis in 1% agarose gel and extraction from the gel using Qiaex Kit C (Qiagen); the purified DNAs were dissolved in 40 µl of TZ buffer.

For the next PCR step, the joining-region heavy chain ($J_H$) forward primer with SfiI site, ACG TTC GGC CCC AGC GGC CCC GCT ACC CCC GCC TCC TGA RGA GAC GGT GAC CRK KGT YCC (SEQ ID NO. 45) were used in combinations with the $V_H$ back-primers listed above. The PCR reagents and conditions were the same as above, except that the primer concentrations were 10 pM and the reaction involved 30 cycles at 94° C. for 1 minute, 50° C. for 1 minute, and 72° C. for 1 minute followed by extension at 72° C. for 10 minutes. The PCR products were purified as above.

The $V_H$ cDNAs and the replicative form of DNA of the fUSE5 vector were digested with SfiI and purified by electrophoresis in 1% low-melting-temperature agarose gel. Ligation of the cDNA with the vector DNA was done in 100 µl of reaction mixture containing 0.8 µg of vector DNA, and 2000 units of $T_4$ DNA ligase for 16 hours t 16° C. The ligation products were purified by extraction with phenol/chloroform and precipitation with ethanol and were dissolved in 20 µl of water. The entire purified DNA sample was used to transform DH10B ElectroMax cells (Gibco/BRL), and the cells were plated on 2×TY agar medium and tetracycline at 12.5 µg/ml in 24×42 cm trays. The size of the library constructed from the PBL of patient DM414 in the vaccination trial at Duke University Medical Center was about 3×10$^8$ independent clones.

Melanoma-specific $V_H$ and scFv antibodies containing $V_H$ domains with distinct CDR3 regions were cloned from the two libraries. The specificities of the antibodies were tested by ELISA and immunohistochemistry with melanoma and other tumor cell lines and primary cultures of three normal cell types, and with frozen sections of metastatic melanoma and normal skin. The antibodies bound only to the melanoma cells in all tests. Thus, both $V_H$ and scFv fusion phage libraries can yield tumor-specific antibodies. Sequence results are set out in SEQ ID NOs 46 to 51.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

The references cited above are hereby incorporated herein in their entireties by reference.

What is claimed is:

1. An antibody H fragment selected from the group consisting of SEQ ID NOs 20, 22, 24, 26, 28, 30, and 32, residues 20 to 119 of SEQ ID NO 34, SEQ ID NOs 36, and 38, and SEQ ID NOs 46 47, 48, 50, and 51.

2. An antibody $V_H$ fragment according to claim 1 which is SEQ ID NO 20.

3. An antibody $V_H$ fragment according to claim 1 which is SEQ ID NO 22.

4. An antibody $V_H$ fragment according to claim 1 which is SEQ ID NO 24.

5. An antibody $V_H$ fragment according to claim 1 which is SEQ ID NO 26.

6. An antibody $V_H$ fragment according to claim 1 which is SEQ ID NO 28.

7. An antibody $V_H$ fragment according to claim 1 which is SEQ ID NO 32.

8. An antibody $V_H$ fragment according to claim 1 which is SEQ ID NO 34.

9. An antibody $V_H$ fragment according to claim 1 which is residues 20 to 119 of SEQ ID NO 36.

10. An antibody $V_H$ fragment according to claim 1 which is SEQ ID NO 36.

11. An antibody $V_H$ fragment according to claim 1 which is SEQ ID NO 38.

12. An antibody $V_H$ fragment according to claim 1 which is SEQ ID NO 46.

13. An antibody $V_H$ fragment according to claim 1 which is SEQ ID NO 47.

14. An antibody $V_H$ fragment according to claim 1 which is SEQ ID NO 48.

15. An antibody $V_H$ fragment according to claim 1 which is SEQ ID NO 50.

16. An antibody $V_H$ fragment according to claim 1 which is SEQ ID NO 51.

* * * * *